United States Patent
Yamamichi et al.

(10) Patent No.: US 7,826,042 B2
(45) Date of Patent: Nov. 2, 2010

(54) RECOGNITION CHIP FOR TARGET SUBSTANCE, AND DETECTION METHOD AND DEVICE FOR THE SAME

(75) Inventors: Junta Yamamichi, Yokohama (JP); Miki Ogawa, Machida (JP); Yoichiro Handa, Yokohama (JP); Takeshi Imamura, Chigasaki (JP); Norihhiko Utsunomiya, Machida (JP); Satoru Nishiuma, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 1059 days.

(21) Appl. No.: 10/571,906

(22) PCT Filed: Mar. 2, 2005

(86) PCT No.: PCT/JP2005/004029
§ 371 (c)(1),
(2), (4) Date: Mar. 14, 2006

(87) PCT Pub. No.: WO2005/085806
PCT Pub. Date: Sep. 15, 2005

(65) Prior Publication Data
US 2009/0009756 A1 Jan. 8, 2009

(30) Foreign Application Priority Data
Mar. 5, 2004 (JP) ............................. 2004-062606
Jun. 25, 2004 (JP) ............................. 2004-188879

(51) Int. Cl.
*G01N 21/27* (2006.01)
*G01N 21/64* (2006.01)

(52) U.S. Cl. .......................... 356/72; 356/317; 356/326; 356/445; 356/246; 435/288.7; 436/164; 436/172
(58) Field of Classification Search ................. 356/301, 356/445
See application file for complete search history.

(56) References Cited

U.S. PATENT DOCUMENTS
5,147,607 A 9/1992 Mochida .................... 422/57
(Continued)

FOREIGN PATENT DOCUMENTS
EP 0 965 835 12/1999
(Continued)

OTHER PUBLICATIONS
Preston, et al., "New Technique for the Determination of Metal Particle Size in Supported Metal Catalysts", Journal of Physical Chemistry, vol. 92, No. 10, May 19, 1988, pp. 2957-2960.

*Primary Examiner*—F. L Evans
(74) *Attorney, Agent, or Firm*—Fitzpatrick, Cella, Harper & Scinto

(57) ABSTRACT

A detection device comprising a substrate comprising a plurality of objects of which properties are changed due to the contact with a target substance, means for bringing the target substance into contact with the objects, and means for detecting a change in properties of the objects caused when the target substance is brought into contact with the objects, based on light output when the objects are irradiated with light, wherein the plurality of objects are located in the direction in which the light for irradiation travels, and the detecting means is means for detecting the change in the properties based on the summation of light output from the plurality of objects upon irradiation with light.

5 Claims, 12 Drawing Sheets

U.S. PATENT DOCUMENTS

| | | | |
|---|---|---|---|
| 5,372,783 A | 12/1994 | Lackie | 422/68.1 |
| 5,759,866 A | 6/1998 | Machida et al. | 436/518 |
| 6,331,276 B1 | 12/2001 | Takei et al. | |
| 6,361,958 B1 | 3/2002 | Shieh et al. | 435/7.1 |
| 6,515,749 B2 | 2/2003 | Pipino | 356/440 |
| 6,531,068 B2 | 3/2003 | Laermer et al. | 216/37 |
| 6,596,078 B2 | 7/2003 | Konakahara et al. | 117/75 |
| 6,970,239 B2 | 11/2005 | Chan et al. | |
| 7,079,250 B2 | 7/2006 | Mukai | 356/445 |
| 2004/0183176 A1* | 9/2004 | Naya et al. | 257/680 |

FOREIGN PATENT DOCUMENTS

| | | |
|---|---|---|
| EP | 1 445 601 | 8/2004 |
| JP | 3-223674 | 10/1991 |
| JP | 9-196920 | 7/1997 |
| JP | 11-326193 A | 11/1999 |
| JP | 2000-263556 | 9/2000 |
| JP | 2000-356587 | 12/2000 |
| JP | 2002-167300 | 6/2002 |
| JP | 2002-365210 | 12/2002 |
| JP | 2003-514221 | 4/2003 |
| JP | 2003-268592 | 9/2003 |
| JP | 2003-268592 A | 9/2003 |
| JP | 2005-524857 | 8/2005 |
| WO | 03/106943 A1 | 12/2003 |

* cited by examiner

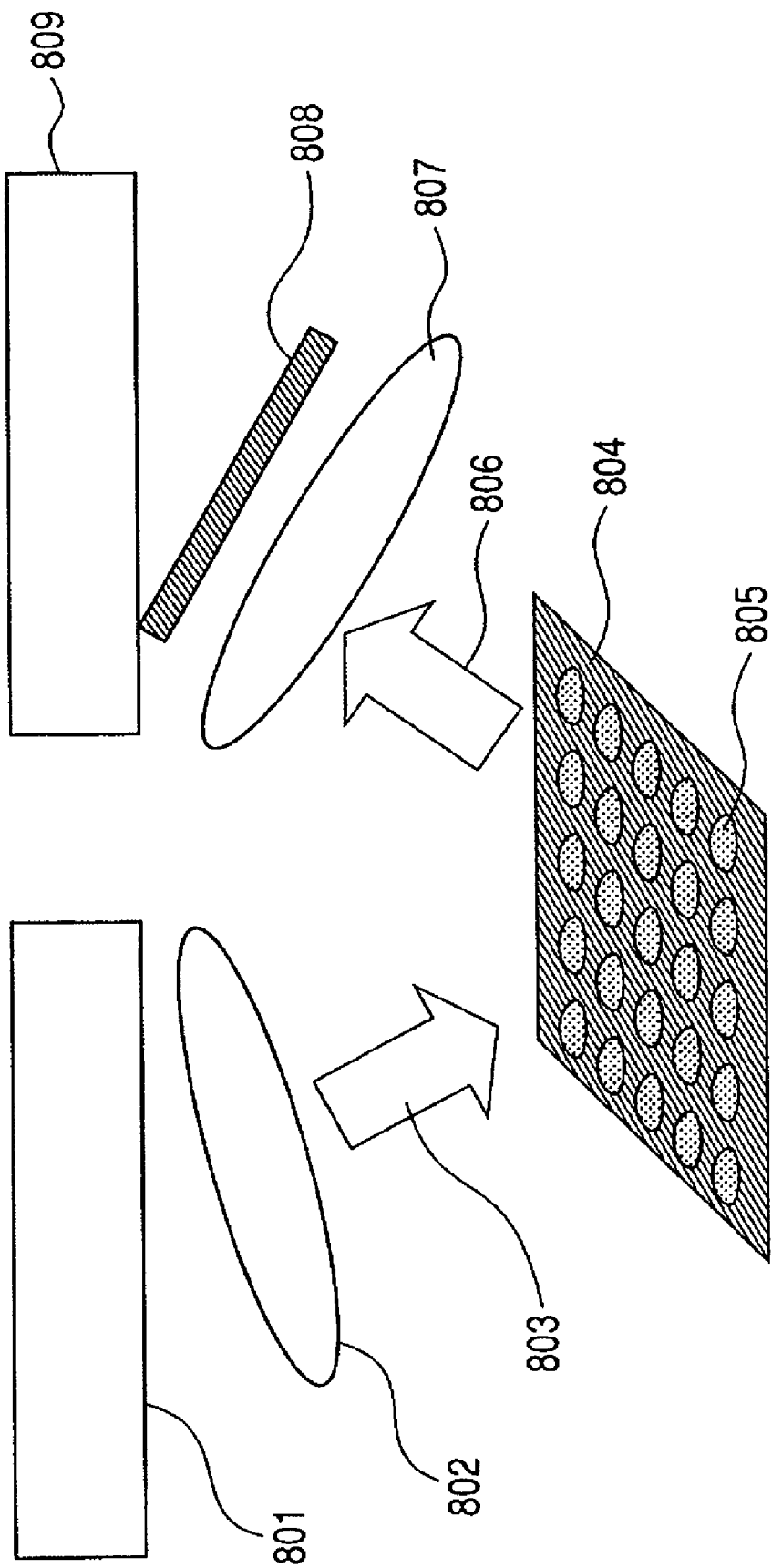

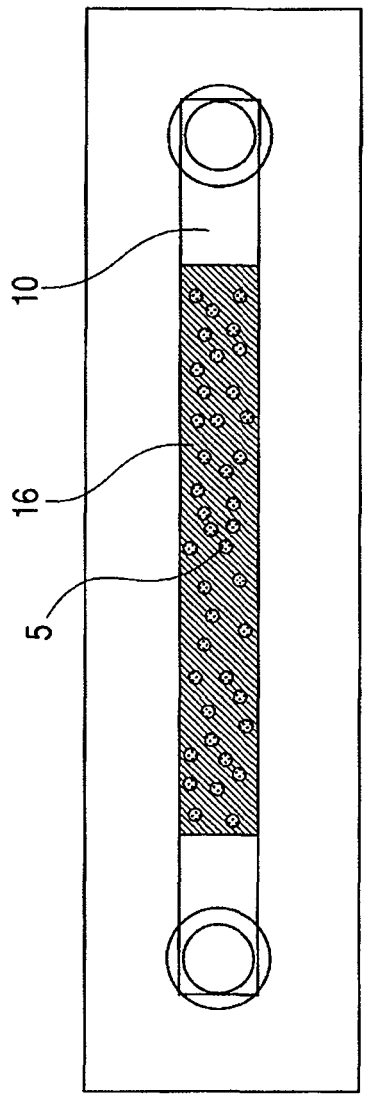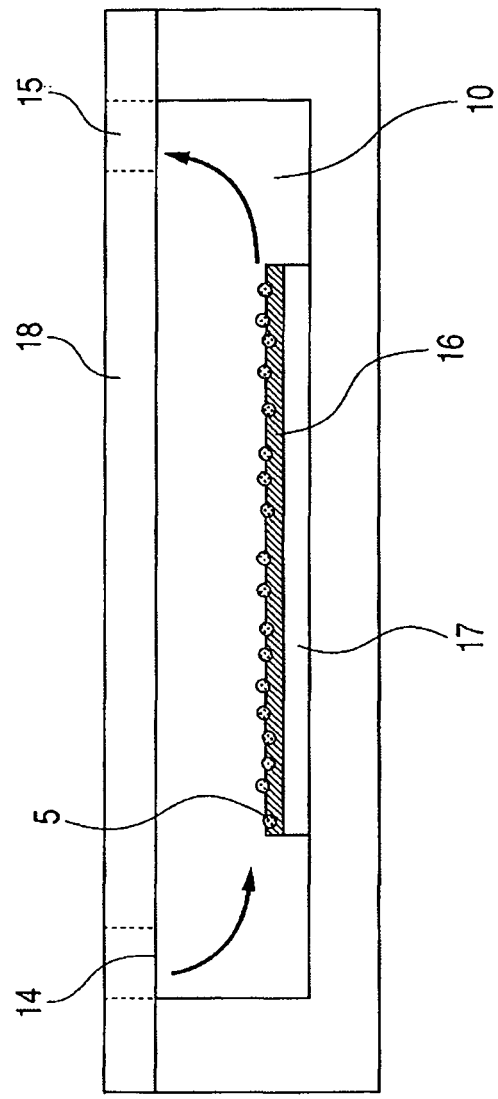
FIG. 13A
FIG. 13B

RECOGNITION CHIP FOR TARGET SUBSTANCE, AND DETECTION METHOD AND DEVICE FOR THE SAME

TECHNICAL FIELD

The present invention relates to a chip for sensitively recognizing a target substance in a sample, a detection device and a detection method.

BACKGROUND ART

In recent years, with increased awareness of problems of health, environment and safety, a technique for detecting a trace biological or chemical substance involved in these problems has been desired.

However, such a substance to be detected (hereinafter may be referred to as "target substance") is often included only in a slight amount in a complicated mixture of various substances, and a specimen comprising such a target substance can be collected only in a limited amount. Therefore, detection and measurement of a target substance require high sensitivity, accuracy and reproducibility.

Further, the specimen is often a specimen derived from an organism (hereinafter referred to as "sample"), and it is difficult to acquire the sample. Thus, detection requiring a smaller amount of the specimen has been demanded. This demand for a smaller amount of the sample is also based on the fact that the sample may be a source of infection after disposal, because it is a specimen derived from an organism.

In terms of applications of human clinical laboratory equipment, reduction in the length of time between the acquisition of a sample and the output of detection results, so-called "turn around time", has been strongly demanded.

As a technique for responding to these demands, a method of improving the reaction efficiency by using a microstructure having a reaction space for trapping a target substance, which is microscopic and has a large surface area per unit volume, has been developed.

Japanese Patent Application Laid-Open No. H03-223674 discloses a reaction vessel for measuring a trace substance in vivo in a simple manner, wherein the reagent fixed parts and/or reagent attached parts formed in a passage through which a fluid flows are concaves and/or small projection aggregates.

Japanese Patent Application Laid-Open No. H09-196920 discloses a body fluid component analyzing instrument having a specimen receiving port, a pump connection port, a specimen treatment region with a specimen labeled with a labeling substance located therein, and a specimen treating and photometric region with a porous material, in which one of a pair of specific bonds is fixed, located therein.

National Publication of International Patent Application No. 2003-514221 discloses a microfluidic device comprising a microchannel for transportation of fluids, wherein the microchannel contains spatially separated defined regions of a specific binding pair member fixed on a porous polymer, beads or microstructures fabricated in the microchannel.

On the other hand, detection methods differing from conventional ones have been now proposed in order to satisfy the above-described demands. Specifically, the detection methods are, as illustrated below, utilize metal-containing microparticles. Metal element-containing microparticles, which have optical characteristics highly sensitive to a slight change in the medium adjacent to the surface of the microparticles, can sensitively recognize a physicochemical change due to the presence of a labeled trace substance.

Japanese Patent Application Laid-Open No. 2000-356587 discloses a localized plasmon resonance sensor which has a sensor unit constituted to have a given substrate and metal microparticles fixed on the surface of the substrate and detects the refractive index of a medium near the metal microparticles by measuring the absorbance of light transmitted through the metal microparticles when the sensor unit is irradiated with light.

Japanese Patent Application Laid-Open No. 2002-365210 discloses a method for detecting living body molecules, characterized in that an apparatus for optically detecting molecular adsorption utilizing optical characteristics of an optical multilayer film, constituted by a substrate, a noble metal thin layer, dielectric microparticles and noble metal microparticles, detects molecular absorption in which, when the optical multilayer film absorbs molecules, the maximum absorption wavelength of the reflection spectrum of the optical multilayer film shifts, but, when the refractive index of a liquid in which the optical multilayer film is immersed changes, the maximum absorption wavelength of the reflection spectrum changes at a level of 1,000 nm or less per unit of the refractive index.

Japanese Patent Application Laid-Open No. 2003-268592 discloses a structure, characterized in that the structure comprises anodized alumina layers, having a plurality of independent pores formed almost perpendicular to the surface of the layers, integrally with mutually isolated metal particles formed with which the respective independent pores are filled, and a sensor, characterized in that the sensor detects the refractive index of a medium near the metal particles fixed on the substrate by measuring the absorbance of light reflected from or transmitted into the metal particles in the structure upon irradiation of the structure with light.

In such a way, various detection chips and devices have now been developed in order to detect a trace target substance. However, it is obvious that a more slight amount of a component must be detected in a short period of time from a small amount of a sample. In addition, it is desirable that clinical laboratory equipment can sensitively detect a trace component as described above and quantitatively measure a component at a high concentration without dilution of a sample.

DISCLOSURE OF THE INVENTION

As a result of extensive studies to solve the above problems, the present inventors have achieved the following invention.

According to an aspect of the present invention, there is provided a detection device comprising:

a substrate comprising a plurality of objects of which properties are changed due to the contact with a target substance, a means for bringing the target substance into contact with the objects, and means for detecting a change in properties of the objects caused when the target substance is brought into contact with the objects, based on light output generated when the objects are irradiated with light, wherein the plurality of the objects are located in the direction in which the light for irradiation travels, and the detecting means is a means for detecting the change in the properties based on the summation of light output from the plurality of the objects upon irradiation with light.

The objects are preferably microparticles containing a metal element.

The objects further preferably comprise a trap for trapping the target substance on the surface, and the target substance is trapped in the trap.

The detecting means is preferably a fluorescence method, an electrochemiluminescence method or a plasmon resonance method.

The device preferably further comprises a channel for transporting the sample.

According to another aspect of the present invention, there is provided a detection method comprising the steps of:

providing a substrate comprising a plurality of objects of which properties are changed due to the contact with a target substance, bringing the target substance into contact with the objects, and detecting a change in properties of the objects caused when the target substance is brought into contact with the objects in the contact step, based on light output when the objects are irradiated with light, wherein the detecting step comprises a detection based on the summation of light output from the plurality of the objects located in the direction in which the light for irradiation travels.

According to a further aspect of the present invention, there is provided a detection chip comprising:

a substrate comprising a plurality of objects of which properties are changed due to the contact with a target substance and a means for bringing the target substance into contact with the objects, wherein a change in properties of the objects caused when the target substance is brought into contact with the objects is detected based on light output generated when the objects are irradiated with light, and the plurality of the objects are located in the direction in which the light for irradiation travels.

The present invention can realize a reaction region composed of a microscopic space by using a microstructure with a large surface area per unit volume. Use of the microstructure can achieve the same effect as in a configuration with microscopic and short reaction channels arranged in parallel, and makes it unnecessary to remarkably increase the pressure when transporting a fluid to a reaction region. Further, since voids in the microstructure are narrow, the diffusion distance can be shortened, and the time requiring for the reaction can be reduced. Moreover, since a structure with microparticles containing a metal element fixed thereon forms the microstructure, the number of microparticles per unit project area during optical detection can increase, and the sensitivity can be improved. In addition, since the microstructure has a large surface area per unit volume, the amount of the microparticles per unit volume is large. Thus, the microparticles can recognize a target substance as a whole even if the target substance is present at a high concentration, which results in a wide dynamic range of the concentrations to be detected.

BRIEF DESCRIPTION OF THE DRAWINGS

FIG. 8 is a view showing the configuration of the detection device in Example 3 of the present invention;

FIGS. 13A and 13B are views showing the configuration of the detection device in Example 5 of the present invention.

BEST MODE FOR CARRYING OUT THE INVENTION

Figure 1A:
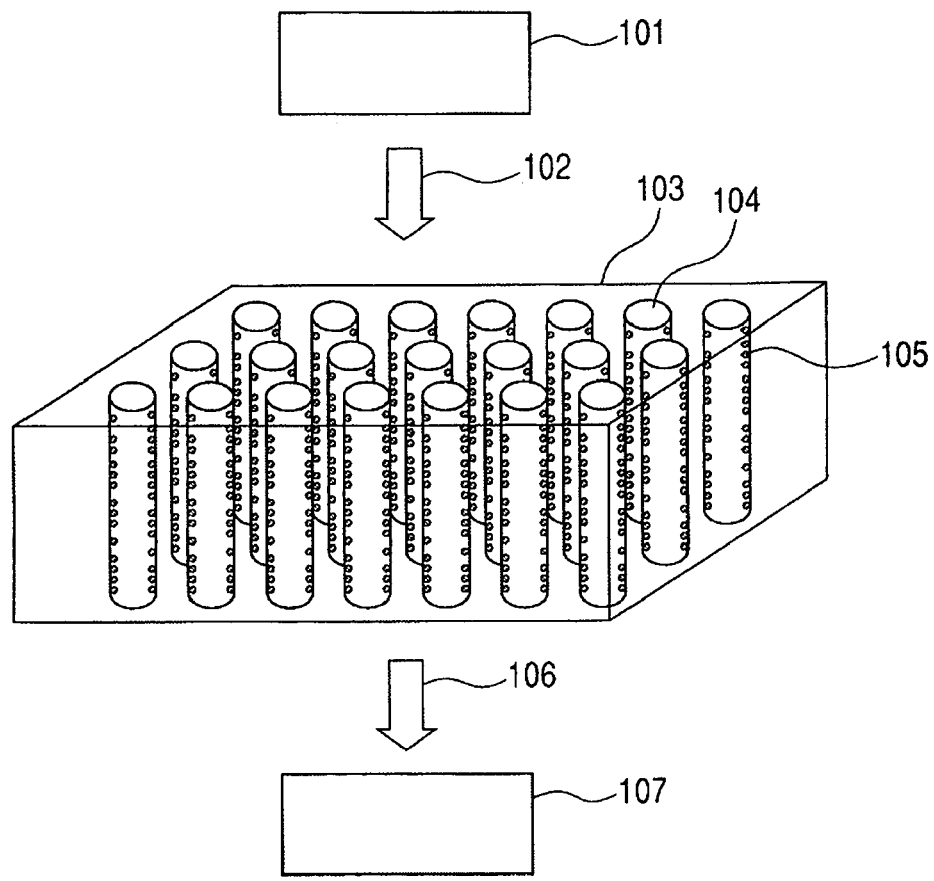
FIGS. 1A, 1B and 1C are general views showing one embodiment of the measuring method using a hollow structure.

The present invention relates to a chip for recognizing a target substance in a sample, characterized in that the recognition chip for the target substance comprises a microstructure and microparticles containing a metal element which are located on at least the surface of the microstructure, and the target substance is recognized when the sample is brought into contact with the microparticles. Further, the detection chip is preferably characterized in that the microparticles can be combined with a trap for trapping a target substance, a target substance is trapped in the trap and thus recognized when a sample is brought into contact with the microparticles, and the detection chip has a plurality of regions with microstructures for recognizing a target substance and further has a channel for transporting a sample.

Furthermore, the detection device for recognizing a target substance of the present invention has a detection chip for recognizing a target substance, comprising a microstructure and microparticles containing a metal element which are located on at least the surface of the microstructure; introduction means for introducing a sample into the detection chip; contact means for bringing the introduced sample into contact with the microparticles; and means for detecting a physical or chemical change caused by bringing the sample into contact with the microparticles. In this case, the detecting means for detecting a physical or chemical change caused by bringing the sample into contact with the microparticles is preferably optical detecting means for optically detecting such a change, and the optical detecting means preferably consists of at least photoirradiation means for irradiating the detection chip with light and photodetecting means for receiving light from the detection chip. The light received by the photodetecting means is, more preferably, light influenced by fluorescence, electrochemical luminescence or plasmon resonance.

The present invention also relates to a method for detecting a target substance, characterized in that the method has a step of introducing a sample into a region comprising a microstructure and microparticles containing a metal element which are located on at least the surface of the microstructure, and a step of detecting a physical or chemical change caused by bringing the sample into contact with the microparticles.

The best embodiment of the present invention will be described in detail with reference to the attached drawings.

The microstructure as a reaction region of the present embodiment refers to a structure composed of any material with voids having a size of about several hundred μm or less each. Examples of the microstructure include a hollow structure (FIG. 1A), a porous structure (FIG. 2A), an opal structure (FIG. 2B), an inverse opal structure (FIG. 2C), a microparticle aggregated structure (in which microparticles in the opal structure are irregularly arranged side-by-side) (not shown), a column structure (FIG. 2D), a convex structure (FIG. 2E), a concave structure (FIG. 2F), a projected structure (FIG. 2G) and a fiber structure (FIG. 2H). Here, detection of a target substance using a hollow structure as the microstructure will be described.

In the present embodiment, a composite of a microstructure as a reaction region and microparticles containing a metal element (hereinafter referred to as "metal element-containing microparticles") is located on a substrate. A trap for a target substance may be fixed on the metal element-containing microparticles. By fixing the trap functioning to complementarily bind to a target substance on the metal element-containing microparticles, the target substance can be fixed on a region near the microparticles, which enables detection with high reproducibility.

The trap need not necessarily be fixed, and it is sufficient if the metal element-containing microparticles have properties that allow recognition of a target substance in a sample. Here, the recognition refers to, for example, detection of a target substance near the metal element-containing microparticles. When a target substance is near the metal element-containing microparticles, the refractive index near the metal element-containing microparticles changes. Since the change in the refractive index appears in absorption and scattering spectra or the like, the target substance can be detected. In such a case, the microparticles can be used for a sensor which detects the refractive index or the like (type or concentration) of a fluid, for example.

Further, a light source and a photodetector necessary for the measurement are located with the reaction region for recognizing a target substance interposed therebetween. In this case, the substrate is preferably a material transparent to light from the light source, e.g. glass. When the microstructure is a hollow structure or porous structure, the pores preferably have a diameter of several ten nm to several ten μm each.

Figure 1B:
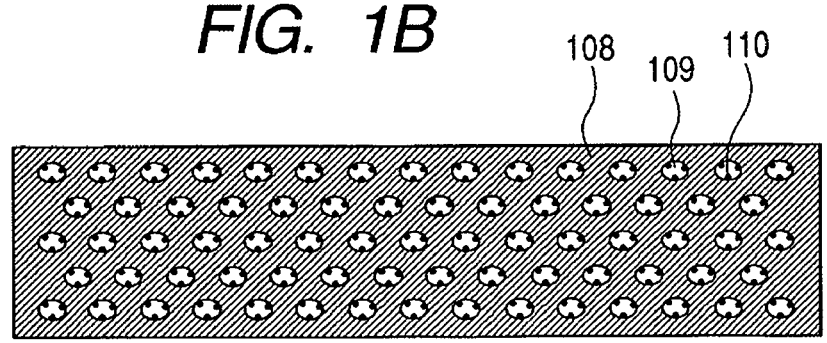

FIG. 1A is a schematic view showing the entire configuration of the detection device; FIG. 1B shows the top surface of a hollow structure as the detection chip, and FIG. 1C shows the side cross-section of a hollow structure.

The measurement system consists of a light source 101, a reaction region (hollow structure) 103 in the chip and a photodetector 107. Light emitted from the light source 101, which is incident light 102, is incident on a reaction region 103 in the chip. In the reaction region 103 in the chip, a plurality of through-holes 104 are formed. The inner surface of the through-holes 104 adsorbs metal element-containing microparticles 105. Transmitted light 106 outgoing from the reaction region 103 in the chip is detected by the photodetector 107.

Figure 1C:
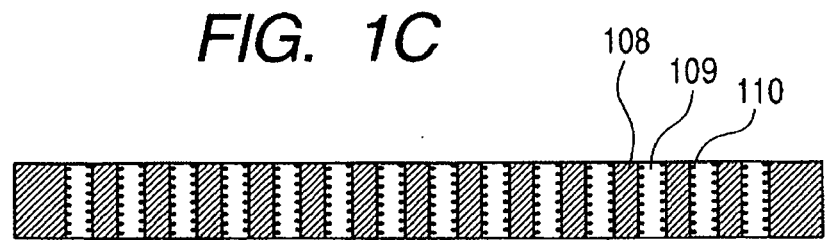

FIGS. 1B and 1C are respectively a top view and a cross-sectional view of the reaction region 103 in the chip. The reference numerals 109 and 110 respectively denote a through-hole 109 which penetrates through a substrate formed on a substrate 108 as the reaction region 103 in the substrate and metal element-containing microparticles 110 adsorbed on the inner surface of the through-hole 104.

The metal element-containing microparticles 105 may be either cohesive or isolated, and have a space sufficient for a desired reaction.

According to FIG. 1A, the incident light 102 from the light source 101 is incident on the top surface of the reaction region 103 in the chip, and the transmitted light 106 from the reaction region 103 in the chip is detected by the photodetector 107. However, it is also possible for the reflected light to be detected by changing the location of the photodetector 107.

Spectral characteristics based on the localized surface plasmon resonance of the metal element-containing microparticles 105 adsorbed on the through-holes 104 can be obtained by measuring the absorption and/or scattering spectra using the photodetector 107. The absorption and/or scattering spectra can be measured by detecting the change in the adsorption and/or scattering spectra caused by changing the medium which is in contact with the surface of the metal element-containing microparticles 105 (more particularly, the medium in a region near the metal element-containing microparticles) or allowing the trap fixed on the metal element-containing microparticles in advance to bind to a target substance.

In the case of using a detection technique based on the localized surface plasmon resonance of the metal element-containing microparticles, the metal element contained in the metal element-containing microparticles may be any metal element that can cause localized surface plasmon resonance. In particular, gold, silver, copper, platinum, aluminum, zinc, potassium and the like are preferable. On the other hand, in the case of using a detection technique based on a fluorescence or electrochemiluminescence method as described below, any metal element suitable for each technique can be selected.

Although the material for the microstructure such as a hollow structure or porous structure can be selected from any materials so that the detection technique and the efficiency in trapping the target substance are optimal, the material is more preferably a material transparent to the wavelengths of the incident light and the light to be detected.

The detection device comprises means for detecting a physical or chemical change caused by bringing a sample into contact with the metal element-containing microparticles, and the amount per unit volume of the metal element-containing microparticles is large. Therefore, the physical or chemical change caused by the presence of a target substance appears in the reaction region at a high level, whereby the detection sensitivity can be improved.

In the case of recognizing the physical/chemical change caused in the microstructure as the reaction region by optical detection, it is not necessary to make a structure for detecting the physical/chemical change directly in the reaction region. Thus, the chip has a simple structure and can be produced in a process over a shorter period of time. Further, since the interval between the reaction region and the detection section can be made longer, the detection device can be designed and manufactured more easily.

As the method for optical detection, a fluorescence method, an electrochemiluminescence method and a plasmon resonance method are preferably used. Since the concentration of a target substance can be determined based on the amount of light in the fluorescence or electrochemiluminescence method, the detection mechanism can be simple. In the case of using the plasmon resonance method, since the physical change during the reaction can be detected, even the status of the reaction process can be used as a parameter for determining the concentration of a target substance. Further, since labeling is not required, the number of the reaction steps in the reaction region can decrease, and the time requiring for the detection can be reduced.

(Microstructure)

The microstructure of the present invention is a structure in which voids are formed so that the structure has a large surface area (specific surface area) per unit volume. The voids in the microstructure of the present invention are designed to have volumes and intervals between them so that the microstructure has a desired specific surface area. The microstructure of the present invention is one constituent material of the trapping chip, detection chip and detection device of the present invention, has voids in which at least the metal element-containing microparticles as a constituent material of the present invention can be located, and further can have a void shape selected taking the properties of a sample comprising a target substance (for example, the amount of the target substance or liquid properties such as viscosity) into consideration. The voids preferably penetrate the structure. The voids preferably have a diameter of 1 nm to 10 μm each. It has been found that, however, the voids more preferably have a minimum diameter of 50 nm or larger each in view of channel resistance, and more preferably have a maximum diameter of 1,000 nm or smaller each in view of the diffusion time in the voids.

The material for the microstructure used in the present invention may be any material that can form the structure of the present invention, and is any one or more materials selected from the group consisting of metals, metal oxides, inorganic semiconductors, organic semiconductors, inorganic solid materials such as glass and ceramics, natural polymers, synthetic polymers, and plastics, or a material comprising a composite thereof.

The microstructure used in the present invention may have any shape that can form the structure of the present invention, and comprises any one or more shapes selected from the group consisting of a porous structure, opal structure, inverse opal structure, microparticle aggregated structure, column structure, hollow structure, convex structure, concave structure, projected structure and fiber structure.

The shapes of the microstructure of the present invention are respectively defined as described below.

Figure 2A:
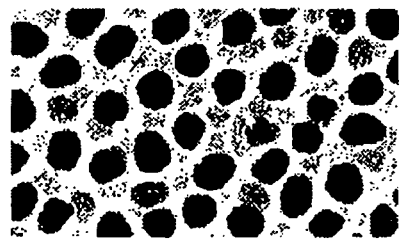
FIGS. 2A, 2B, 2C, 2D, 2E, 2F, 2G and 2H show a microstructure.

Porous structure: A structure having many holes each with any shape opening at random (FIG. 2A)

Figure 2B:
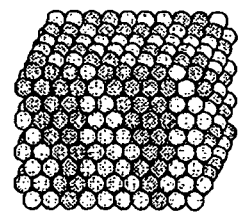

Opal structure: A structure in which spheres are closely accumulated (FIG. 2B)

Figure 2C:
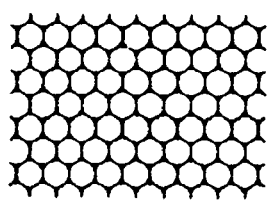

Inverse opal structure: A structure in which a space corresponding to the space portion of the opal structure is filled with a substance (FIG. 2C)

Microparticle aggregated structure: A structure in which spheres are not closely accumulated (not shown)

Figure 2D:
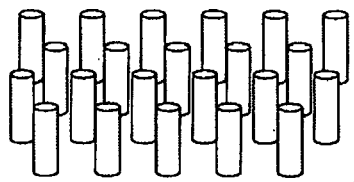

Column structure: A structure in which many columns with any shape are arranged side-by-side (FIG. 2D)

Hollow structure: A structure in which a plurality of through-holes are formed (FIGS. 1A, 1B and 1C)

Figure 2E:
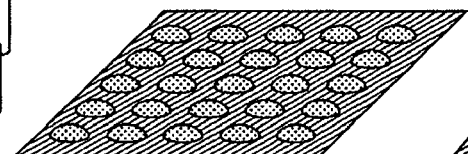
Figure 2F:
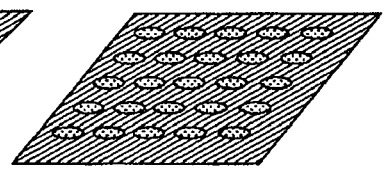
Figure 2G:
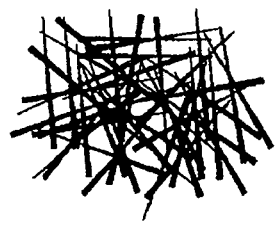
Figure 2H:
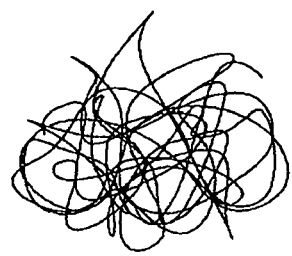

Convex structure: A structure in which a plurality of convex projections with any shape (a shape like a convex lens in FIG. 2E) are on a substrate Concave structure: A structure in which a plurality of concave holes with any shape (a shape like a concave lens in FIG. 2F) are on a substrate Projected structure: A structure in which many needle-like projections are entangled with each other (FIG. 2G)

Fiber structure: A structure in which many fibrous components are entangled with each other in a complicated manner (FIG. 2H)

Given as the organic polymer compound as a main component of plastics is an organic polymer compound produced by polymerization of one or more polymerizable monomers selected from the group consisting of styrene polymerizable monomers such as styrene, α-methylstyrene, β-methylstyrene, o-methylstyrene, m-methylstyrene, p-methylstyrene, 2,4-dimethylstyrene, p-n-butylstyrene, p-tert-butylstyrene, p-n-hexylstyrene, p-n-octylstyrene, p-n-nonylstyrene, p-n-decylstyrene, p-n-dodecylstyrene, p-methoxystyrene and p-phenylstyrene; acrylic polymerizable monomers such as methyl acrylate, ethyl acrylate, n-propyl acrylate, isopropyl acrylate, n-butyl acrylate, isobutyl acrylate, tert-butyl acrylate, n-amyl acrylate, n-hexyl acrylate, 2-ethylhexyl acrylate, n-octyl acrylate, n-nonyl acrylate, cyclohexyl acrylate, benzyl acrylate, dimethyl phosphate ethyl acrylate, diethyl phosphate ethyl acrylate, dibutyl phosphate ethyl acrylate and 2-benzoyloxyethyl acrylate; methacrylic polymerizable monomers such as methyl methacrylate, ethyl methacrylate, n-propyl methacrylate, isopropyl methacrylate, n-butyl methacrylate, isobutyl methacrylate, tert-butyl methacrylate, n-amyl methacrylate, n-hexyl methacrylate, 2-ethylhexyl methacrylate, n-octyl methacrylate, n-nonyl methacrylate, diethyl phosphate ethyl methacrylate and dibutyl phosphate ethyl methacrylate; methylene aliphatic monocarboxylates; and vinyl polymerizable monomers such as vinyl esters such as vinyl acetate, vinyl propionate, vinyl benzoate, vinyl butyrate, vinyl benzoate and vinyl formate, vinyl ethers such as vinyl methyl ether, vinyl ethyl ether and vinyl isobutyl ether, and vinyl ketones such as vinyl methyl ketone, vinyl hexyl ketone and vinyl isopropyl ketone.

Examples of the inorganic solid material that can be used include, but are not limited to, naturally, clay minerals such as kaolinite, bentonite, talc and mica; metal oxides such as alumina, titania, zinc oxide, magnetite, ferrite, NbTa composite oxide, $WO_3$, $In_2O_3$, $MoO_3$, $V_2O_5$ and $SnO_2$; insoluble inorganic salts such as silica gel, hydroxyapatite and calcium phosphate gel; metals such as gold, silver, platinum and copper; semiconductor compounds such as GaAs, GaP, ZnS, CdS and CdSe; glass, silicon and composites thereof.

The microstructure of the present invention may be formed as a membrane or sheet using a film made of plastics such as polyethylene terephthalate (PET), diacetate, triacetate, cellophane, celluloid, polycarbonate, polyimide, polyvinyl chloride, polyvinylidene chloride, polyacrylate, polyethylene, polypropylene or polyester; a porous polymer membrane made of polyvinyl chloride, polyvinyl alcohol, acetyl cellulose, polycarbonate, nylon, polypropylene, polyethylene, Teflon or the like; a wooden board, a glass-plate, a silicon substrate; a fabric of cotton, rayon, an acrylic resin, silk, polyester or the like; or paper such as woodfree paper, wood containing paper, art paper, bond paper, recycled paper, baryta paper, cast coated paper, corrugated paper or resin coated paper. However, the shape of the microstructure is not limited thereto, naturally. These membrane or sheet-like materials may be smooth or uneven.

Examples of the microstructure include, but are not limited to, a substrate of silicon, silica, glass, quartz glass or the like and microgrooves and holes in such a substrate processed by a technique such as photolithography, etching or sandblast; a column structure, a projected structure, a concave structure, a convex structure, a dome-like structure or such a structure having a surface processed with a thin film of gold, silver or platinum; a substrate of PDMS (polydimethylsiloxane), PMMA (polymethyl methacrylate), PET (polyethylene terephthalate), PC(polycarbonate), PS (polystyrene) or the like and microgrooves and holes in such a substrate processed by a forming technology; a column structure, a projected structure, a concave structure, a convex structure, a dome-like structure, a carbon nanotube, a carbon nanohorn, fullerene diamond or an aggregate thereof; nanowhiskers made of alumina, carbon, fullerene, ZnO or the like; a mesoporous thin film, microparticles and a monolith structure made of $SiO_2$, aluminosilicate, other metallosilicates, $TiO_2$, $SnO_2$, $Ta_2O_5$ or the like; microparticles of gold, silver, copper, platinum or the like; microparticles of iron oxide such as magnetite, ferrite, hematite, γ-hematite or maghemite; an aluminum-silicon mixed membrane and a silicon oxide nanostructure obtained by anodizing the membrane, a porous alumina thin film, an alumina nanohole structure, a silicon nanowire or the like.

The microstructure is not limited to the above-described structures and materials.

(Object of which Properties are Changed Due to the Contact with a Target Substance)

Examples of the object of which properties are changed due to the contact with a target substance include microparticles containing a metal element. The metal element-containing microparticles may contain any metal element such as an alkali metal element such as potassium, gold, silver, copper, platinum, zinc, lithium or aluminum; an alkaline earth metal element, beryllium, or magnesium; a metal with magnetic properties such as iron, cobalt or nickel; or a semiconductor element such as scandium, titanium, vanadium, chromium, manganese, gallium or germanium. Preferable examples include, but are not limited to, elements that easily cause plasmon resonance such as gold, silver, copper, aluminum, zinc and potassium.

(Target Substance/Target Substance Trap)

Target substances to be included in a sample are roughly classified into xenobiotic substances and biological substances.

Xenobiotic substances that are industrially advantageous include PCBs with different numbers/positions of chlorine substituents as environmental pollutants, dioxins with different numbers/positions of chlorine substituents as environmental pollutants and endocrine disrupting chemicals that are called environmental hormones (for example, hexachlorobenzene, pentachlorophenol, 2,4,5-trichloroacetic acid, 2,4-dichlorophenoxyacetic acid, amitrole, atrazine, alachlor, hexachlorocyclohexane, ethyl parathion, chlordane, oxychlordane, nonachlor, 1,2-dibromo-3-chloropropane, DDT, kelthane, aldrin, endrin, dieldrin, endosulfan (benzoepin), heptachlor, heptachlor epoxide, malathion, methomyl, methoxychlor, mirex, nitrofen, toxaphene, trifluralin, alkyl phenol (with 5 to 9 carbon atoms), nonyl phenol, octylnonyl phenol, 4-octyl phenol, bisphenol A, di-2-ethylhexyl phthalate, butyl benzyl phthalate, di-n-butyl phthalate, dicyclohexyl phthalate, diethyl phthalate, benzo(a)pyrene, 2,4-dichlorophenol, di-2-ethylhexyl adipate, benzophenone, 4-nitrotoluene, octachlorostyrene, aldicarb, benomyl, kepone (chlordecone), manzeb (mancozeb), maneb, metiram, metribuzin, cypermethrin, esfenvalerate, fenvalerate, permethrin, vinclozolin, zineb, ziram, dipentyl phthalate, dihexyl phthalate and dipropyl phthalate).

Biological substances include a biological substance selected from the group consisting of nucleic acids, proteins, sugar chains, lipids and composites of these. More particularly, such a biological substance comprises a biomolecule selected from the group consisting of nucleic acids, proteins, sugar chains and lipids. Specifically, the present invention can be applied to any substance comprising a substance selected from the group consisting of DNAs, RNAs, aptamers, genes, chromosomes, cell membranes, viruses, antigens, antibodies, lectins, haptens, hormones, receptors, enzymes, peptides, glycosphingolipids and sphingolipids. Further, bacteria or cells that produce the above "biological substances" may be target substances as "biological substances" to which the present invention is directed.

Specific proteins include so-called disease markers.

Examples of the disease markers include α-fetoprotein (AFP) as an acidic glycoprotein that is produced in the liver cells during the fetal period and is present in the fetal blood, and as a marker for hepatocellular carcinoma (primary liver cancer), hepatoblastoma, metastatic liver cancer and a yolk sac tumor; PIVKA-II as an abnormal prothrombin appearing in the case of hepatocyte dysfunction, which is confirmed to appear specifically in hepatocellular carcinoma; BCA225 as a glycoprotein that is an immunohistochemically breast cancer-specific antigen, and as a marker for primary and advanced breast cancer, recurrent breast cancer and metastatic breast cancer; basic fetoprotein (BFP) as a basic fetoprotein discovered in a serum, a intestine tissue extract and a brain tissue extract of the human fetus, and as a marker for ovarian cancer, a testis tumor, prostate cancer, pancreatic cancer, biliary tract cancer, hepatocellular carcinoma, renal cancer, lung cancer, stomach cancer, bladder-cancer and colon cancer; CA15-3 as a carbohydrate antigen which is a marker for advanced breast cancer, recurrent breast cancer, primary breast cancer and ovarian cancer; CA19-9 as a carbohydrate antigen which is a marker for pancreatic cancer, biliary tract cancer, stomach cancer, liver cancer, colon cancer and ovarian cancer; CA72-4 as a carbohydrate antigen which is a marker for ovarian cancer, breast cancer, colorectal cancer, stomach cancer and pancreatic cancer; CA125 as a carbohydrate antigen which is a marker for ovarian cancer (in particular, serous cystadenocarcinoma), adenocarcinoma of the corpus uteri, fallopian tube cancer, adenocarcinoma of the uterine cervix, pancreatic cancer, lung cancer and colon cancer; CA130 as a glycoprotein which is a marker for epithelial ovarian cancer, fallopian tube cancer, lung cancer, hepatocellular carcinoma and pancreatic cancer; CA602 as a core protein antigen which is a marker for ovarian cancer (in particular, serous cystadenocarcinoma), adenocarcinoma of the corpus uteri and adenocarcinoma of the uterine cervix; CA54/61 (CA546) as a nuclear matrix sugar chain related antigen which is a marker for ovarian cancer (in particular, mucinous cystadenocarcinoma), adenocarcinoma of the uterine cervix and adenocarcinoma of the corpus uteri; carcinoembryonic antigen (CEA) which is now most widely used for assisting cancer diagnosis as a marker antigen related to tumors such as colon cancer, stomach cancer, rectal cancer, biliary tract cancer, pancreatic cancer, lung cancer, breast cancer, uterine cancer and urinary system cancer; DUPAN-2 as a carbohydrate antigen which is a marker for pancreatic cancer, biliary tract cancer, hepatocellular carcinoma, stomach cancer, ovarian cancer and colon cancer; elastase 1 as a pancreatic exocrine protease which exists in the pancreas and specifically hydrolyzes an elastic fiber, elastin, of the connective tissue (which constitutes the artery wall, tendon or the like), and as a marker for pancreatic cancer, pancreatic cystic adenocarcinoma and biliary tract cancer; immunosuppressive acidic protein (IAP) as a glycoprotein that exists in high concentration in the ascites or serum of the human cancer patient, and as a marker for lung cancer, leukemia, esophageal cancer, pancreatic cancer, ovarian cancer, renal cancer, bile duct cancer, stomach cancer, bladder cancer, colon cancer, thyroid cancer and malignant lymphoma; NCC-ST-439 as a carbohydrate antigen which is a marker for pancreatic cancer, biliary tract cancer, breast cancer, colon cancer, hepatocellular carcinoma, lung adenocarcinoma and stomach cancer; γ-seminoprotein (γ-Sm) as a glycoprotein which is a marker for prostate cancer; prostate specific antigen (PSA) as a glycoprotein extracted from the human prostate tissue, which exists in the prostate tissue and is therefore a marker for prostate cancer; prostate acidic phosphatase (PAP) as an enzyme secreted from the prostate and hydrolyzing a phosphoric ester under acidic pH conditions, which is used as a tumor marker for prostate cancer; nerve specific enolase (NSE) as a glycolytic enzyme that exists specifically in the nerve tissue and neuroendocrine cells, and as a marker for lung cancer (in particular, lung small cell cancer), neuroblastoma, a nerve tumor, pancreas islet cancer, esophagus small cell cancer, stomach cancer, renal cancer and breast cancer; squamous cell carcinoma related antigen (SCC antigen) as a protein extracted and purified from the liver metastatic focus of uterine cervix squamous cell carcinoma, which is a marker for uterine cancer (cervix squamous cell carcinoma), lung cancer, esophageal cancer, head and neck cancer and skin cancer; sialyl Le$^x$-i antigen (SLX) as a carbohydrate antigen which is a marker for lung adenocarcinoma, esophageal cancer, stomach cancer, colon cancer, rectal cancer, pancreatic cancer, ovarian cancer and uterine cancer; Span-1 as a carbohydrate antigen which is a marker for pancreatic cancer, biliary tract cancer, liver cancer, stomach cancer and colon cancer; tissue polypeptide antigen (TPA) as a marker for esophageal cancer, stomach cancer, colorectal cancer, breast cancer, hepatocellular carcinoma, biliary tract cancer, pancreatic cancer, lung cancer and uterine cancer, which is a single chain polypeptide that identifies advanced cancer in combination with other tumor markers, in particular, and is useful for relapse prediction and treatment follow-up; sialyl Tn antigen (STN) as a nuclear matrix carbohydrate antigen, which is a marker for ovarian cancer, metastatic ovarian cancer, stomach cancer, colon cancer, biliary tract cancer, pancreatic cancer and lung cancer; CYFRA (cytokeratin) as a tumor marker effective for detecting lung non-small cell cancer, in particular, lung squamous cell carcinoma; pepsinogen (PG) as an inactive precursor for two pepsines (PGI, PGII) that are protein digestive enzymes secreted into the gastric juice, and as a marker for gastric ulcer (in particular, lower gastric ulcer), duodenal ulcer (in particular, recurrent and intractable duodenal ulcers), Brunner's gland adenoma, Zollinger-Ellison syndrome and acute gastritis; C-reactive protein (CRP) as an acute phase response protein that mutates by a tissue disorder or infection, of which the level is high when myocardial necrosis occurs due to acute myocardial infarction or the like; serum amyloid A protein (SAA) as an acute phase response protein that mutates by a tissue disorder or infection; myoglobin as a hemoprotein with a molecular weight of about 17,500 that exists mainly in the myocardium and skeletal muscle, which is a marker for acute myocardial infarction, myodystrophy, polymyositis and dermatomyositis; creatine kinase (CK) (three kinds of isozyme of CK-MM derived from skeletal muscle, CK-BB derived from brain or smooth muscle and CK-MB derived from myocardium, and CKs (macro CKs) that bind to mitochondrial isozyme or immunoglobulin:) as an enzyme that exists mainly in the soluble fraction of skeletal muscle and myocardium and is released into the blood by cell injury, which is a marker for acute myocardial infarction, hypothyroidism, progressive myodystrophy and polymyositis; troponin T as a protein with a molecular weight of 39,000 that forms a troponin composite together with troponin I, C on a thin filament of striated muscle and is involved in the regulation of muscle contraction, which is a marker for rhabdomyolysis, myocarditis, myocardial infarction and renal failure; cardiac myosin light chain I as a protein included in the cells of skeletal muscle and the cells of myocardium, which is a marker for acute myocardial infarction, myodystrophy and renal failure because the results in which the value of the marker increases indicate dysfunction or necrosis of skeletal muscle or myocardium; and chromogranin A, thioredoxin, 8-OHdG and cortisol that have attracted attention as stress markers in recent years.

The "antibody" as a trap in the present invention refers to an immunoglobulin that is produced in an organism in the natural environment or entirely or partially synthesized by gene recombination technology, protein engineering, organic reaction or the like. The "antibody" in the present invention also includes any derivative having specific binding capacity. This term further includes any protein having a binding domain that is homologous or highly homologous to the binding domain of immunoglobulin (including a chimeric antibody and a humanized antibody). These "antibodies" or "immunoglobulins" are produced in an organism in the natural environment, or entirely or partially synthesized and modified.

The "antibody" or "immunoglobulin" may be a monoclonal antibody or polyclonal antibody specific to a target substance.

The "antibody" or "immunoglobulin" may be a member of any immunoglobulin class, and includes any human class (IgG, IgM, IgA, IgD and IgE). In the present invention, derivatives of the IgG class are more preferable.

The "antibody fragment" in the present invention refers to any molecule or composite of the antibody with a length smaller than the full length of the antibody or immunoglobulin, or any composite of such molecules. Preferably, the antibody fragment has a part important for the specific binding capacity of the full-length antibody. Examples of the antibody fragment include, but are not limited to, Fab, Fab', F(ab')2, scFv, Fv, diabody and Fd fragments.

The antibody fragment may be produced by any means. For example, the antibody fragment may be enzymatically or chemically produced by fragmentation of an intact antibody, or may be recombinantly produced from a gene encoding a partial antibody sequence. Alternatively, the antibody fragment may be entirely or partially synthetically produced. The antibody fragment may be, as required, a single chain antibody fragment. Alternatively, the fragment may comprise a plurality of chains connected by, for example, a disulfide (—S—S—) bond. The fragment may also be a composite of multiple molecules, as required. A functional antibody fragment comprises typically at least about 50 amino acids, and more typically at least about 200 amino acids.

The "variable domain" in the present invention refers to a domain at the end of the immunoglobulin having amino acid sequences that differ according to each antigen in order to specifically bind to/trap each type of the target substance (antigen), and is usually referred to as Fv.

The Fv consists of a "heavy chain variable domain (hereinafter may be referred to as VH)" and a "light chain variable domain (hereinafter may be referred to as VL)". The immunoglobulin G typically comprises two VH domains and two VL domains.

The "functional part in the variable domain of the immunoglobulin heavy chain or light chain (hereinafter may be simply referred to as "functional part")" refers to a part of the variable domain actually specific to a target substance (antigen), and also a part academically called CDR (complementarity determining region: hypervariable region) and, in particular, a part of CDR actually specific to a target substance (antigen).

Any interaction of a target substance with the trap is possible, insofar as the chip of the present invention can detect the amount of a physical/chemical change before and after the binding. More preferably, such interaction is an "antigen-antibody reaction", an "antigen-aptamer (RNA fragment with a specific structure)", a "ligand-receptor interaction", a "DNA hybridization", a "DNA-protein (such as a transcription factor) interaction", a "lectin-sugar chain interaction" or the like.

(Microchannel)

Although the reaction region of the chip of the present invention can be used singly in a batch system reaction, the reaction region can be configured to be connected with a microchannel, and/or the reaction region can be configured to be located in a microchannel, in order to promote a target substance trapping reaction, ensure quantitativeness and reproducibility, and simplify a complicated operation by persons.

The microchannel of the present invention may be processed as a microgroove in the substrate or may have a capillary structure.

As a material for composing the microchannel of the present invention, any materials that allow the microchannel to be processed, allow a sample to be introduced in the target substance trapping reaction region, and do not inhibit the detection system can be used. Typically, inorganic materials such as glass, quartz glass and silicon and resins such as PMMA (polymethyl methacrylate) and PDMS (polydimethylsiloxane), which are fabricated and, if necessary, joined together, or glass, polyimide, fused silica and the like processed as a capillary can be used.

EXAMPLES

The present invention will be described below with reference to other examples. However, these examples should not limit the scope of the present invention.

Example 1

First, the configuration in Example 1 will be described with reference to FIG. 3.

<Configuration>

Figure 3:
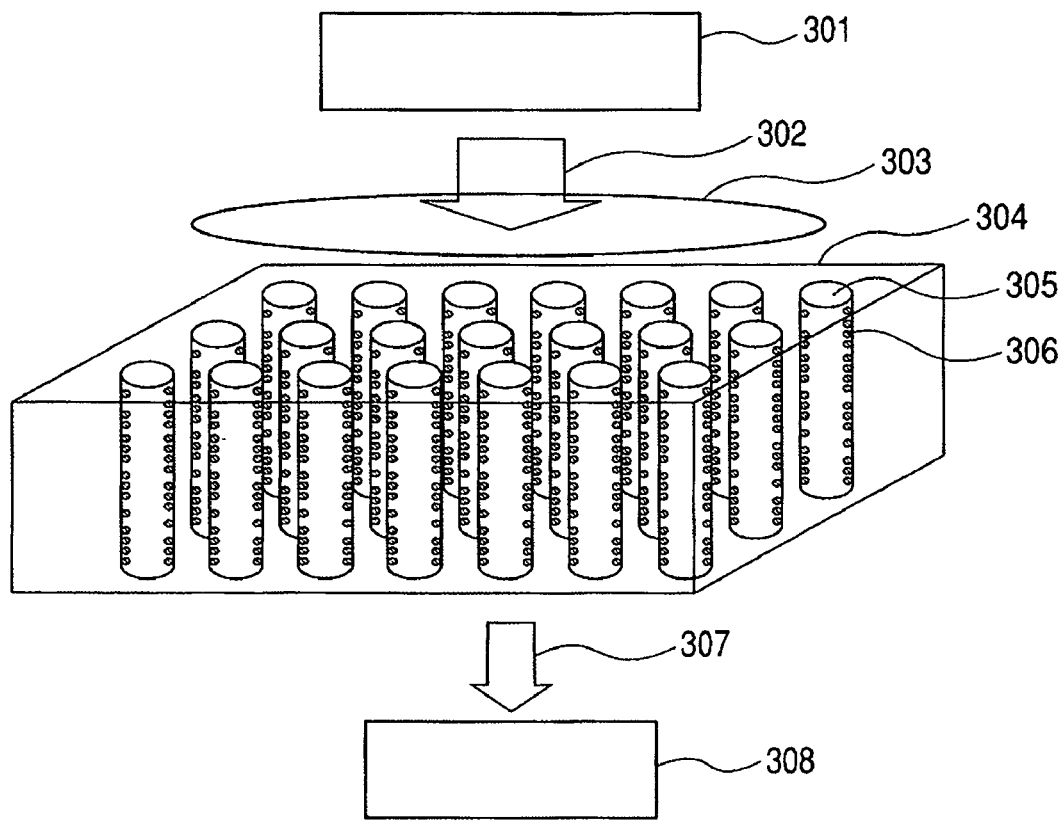
FIG. 3 is a view showing the configuration of the detection device in Example 1 of the present invention.

FIG. 3 is a schematic view showing the configuration in this example. The detection device in FIG. 3 for detecting a target-substance in a sample consists of a tungsten lamp 301, a collimator lens 303, a reaction region 304 in the chip and a spectrophotometer 308. Although the tungsten lamp 301 which generates white light is used in this example, a laser beam may also be used. Incident light 302 emitted from the tungsten lamp 301 is converted into parallel light by the collimator lens 303, and is incident on the reaction region 304 in the chip as a hollow structure with a plurality of through-holes 305 formed on a substrate.

In the through-holes 305 formed in the reaction region 304 as a hollow structure in the chip, gold microparticles 306 are fixed. The incident light 302 is transmitted through the reaction region 304 in the chip as a hollow structure, and exits the reaction region 304 in the chip as outgoing light 307. The outgoing light 307 is incident on the spectrophotometer 308.

Here, the detailed configuration of the detection chip will be described with reference to FIGS. 4A, 4B and 4C.

Figure 4A:
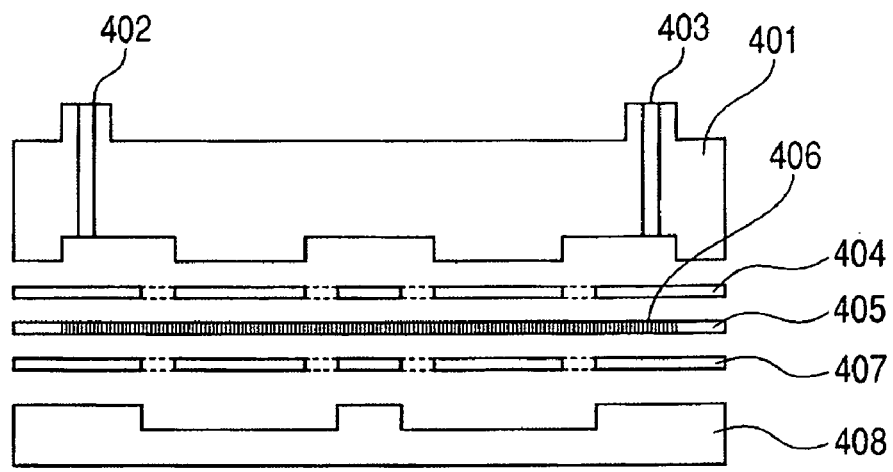
FIGS. 4A, 4B and 4C are views showing the configuration of the detection chip in Example 1 of the present invention.

FIG. 4A is an exploded view in which the detection chip is exploded into constituent components. The detection chip is formed by a top cover 401, a membrane with micropores 406, a packing material 404, a packing material 407, an O-ring 405 and a bottom cover 408. There are no specific limitations to the material for the top cover 401 and the bottom cover 408, insofar as the material is optically transparent, does not allow a fluid to permeate therethrough, and can be formed easily. In the top cover 401, an inlet 402 for introducing a sample and an outlet 403 for discharging the sample after the reaction are formed. The packing materials 404 and 407 are provided in order to allow a fluid to permeate through only the reaction region. The material is not limited insofar as the material has high flexibility, can be formed easily, and does not allow a fluid to permeate therethrough. The O-ring 405 is provided in order to prevent leakage of a fluid from the membrane 406, and is preferably made of silicon rubber or fluorine rubber. The porous membrane 406 used in this example is an alumina nanohole membrane with a hollow structure having through-holes perpendicular to the plane of the membrane.

In this example, the top cover 401 and the bottom cover 408 are formed by molding a PMMA resin, and the packing materials 404 and 407 are formed by molding a PMMA resin. The porous membrane 406 employs nanodisk membrane which is an alumina nanohole membrane manufactured by Whatman plc.

Figure 4B:
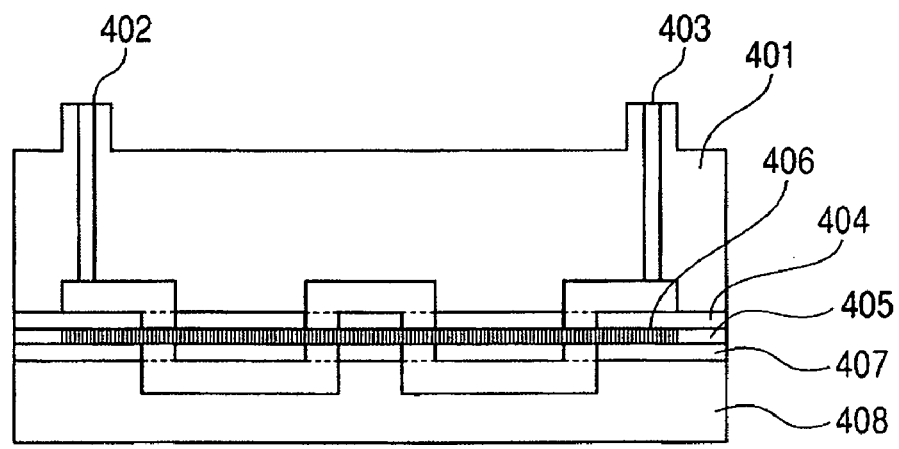

FIG. 4B is a view showing an assembly in which the components in FIG. 4A are vertically combined, and are vertically secured with bolts not shown in the figure at a given force or stronger.

The concavity and convexity formed in the top cover 401 and the bottom cover 408 forms a channel for a sample, and the membrane 406 with micropores, the packing material 404, the packing material 407 and the O-ring 405 form micropores in the channel.

The concavity and convexity formed in the top cover 401 and the bottom cover 408 forms a channel for a sample, and the membrane 406 with micropores, the packing material 404, the packing material 407 and the O-ring 405 form micropores in the channel.

Figure 4C:
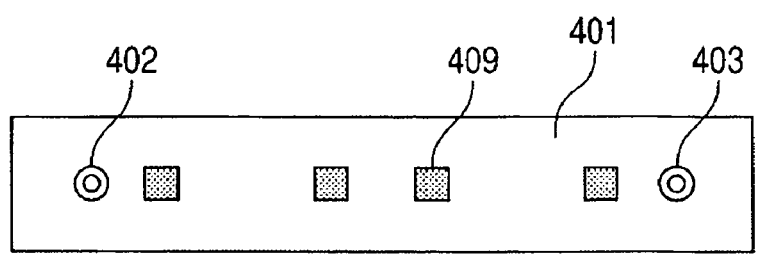

FIG. 4C is a view of the detection chip from the top surface, and a measuring site 409 corresponds to the position of micropores exposed to the channel of the membrane formed with the channel.

The micropores have a diameter of 0.2 μm each, a density of about 8 pores/μm$^2$, and a depth of 60 μm each.

<Method for Preparing Reaction Region>

In order to prepare the reaction region, since it is not necessary to use the whole alumina nanohole membrane as the reaction region, the alumina membrane is sandwiched between the packing materials 404 and 407 and treated, so that the regions other than the reaction region of the alumina membrane are not treated.

First, in this example, gold microparticles were used. The gold microparticles are fixed as follows. The alumina nanohole membrane sandwiched by the packing materials is immersed in a solution of aminoethanethiol, having a thiol group to be bonded to a metal oxide, in ethanol, for the alumina surface of the reaction region. Next, the membrane is immersed in an aqueous solution of gold microparticles with a particle diameter of 20 to 40 nm each (manufactured by Tanaka Kikinzoku Kogyo K.K.), so that the gold microparticles are adsorbed on the hollow columns.

An antibody is then fixed on the gold microparticles as a trap. The fixing method involves surface modification of the gold microparticles fixed on the alumina nanohole membrane using a solution of 11-mercaptoundecanoic acid, with a thiol group having a high affinity to gold, in ethanol. In this case, a predetermined amount of the solution is added dropwise to only the reaction region using a spotter or the like. A carboxyl group is thus exposed on the surface of the gold microparticles. In this state, an aqueous solution of N-hydroxysulfosuccinimide (manufactured by Dojindo Laboratories) and an aqueous solution of 1-ethyl-3-[3-dimethylamino]propyl]carbodiimide hydrochloride (manufactured by Dojindo Laboratories) are added dropwise to the reaction region using a spotter in the same manner. A succinimide group is thus exposed on the surface of the gold microparticles. Subsequently, the hollow columns are immersed in a phosphate buffer (pH 8.0) of a rabbit anti-mouse IgG antibody specific to a target substance as an antibody to be fixed. The rabbit anti-mouse IgG antibody is fixed on the gold surface by reacting the succinimide group located on the gold surface with an amino group of the rabbit anti-mouse IgG antibody. Here, a method of fixing only one antibody has been described. When different antibodies are to be fixed on each reaction region, reaction regions for the chip to which a plurality of antibodies are fixed can be prepared by masking the regions other than the objective reaction region and changing the antibody to be fixed to repeat the same treatment.

<Detection Method>

Figure 5:
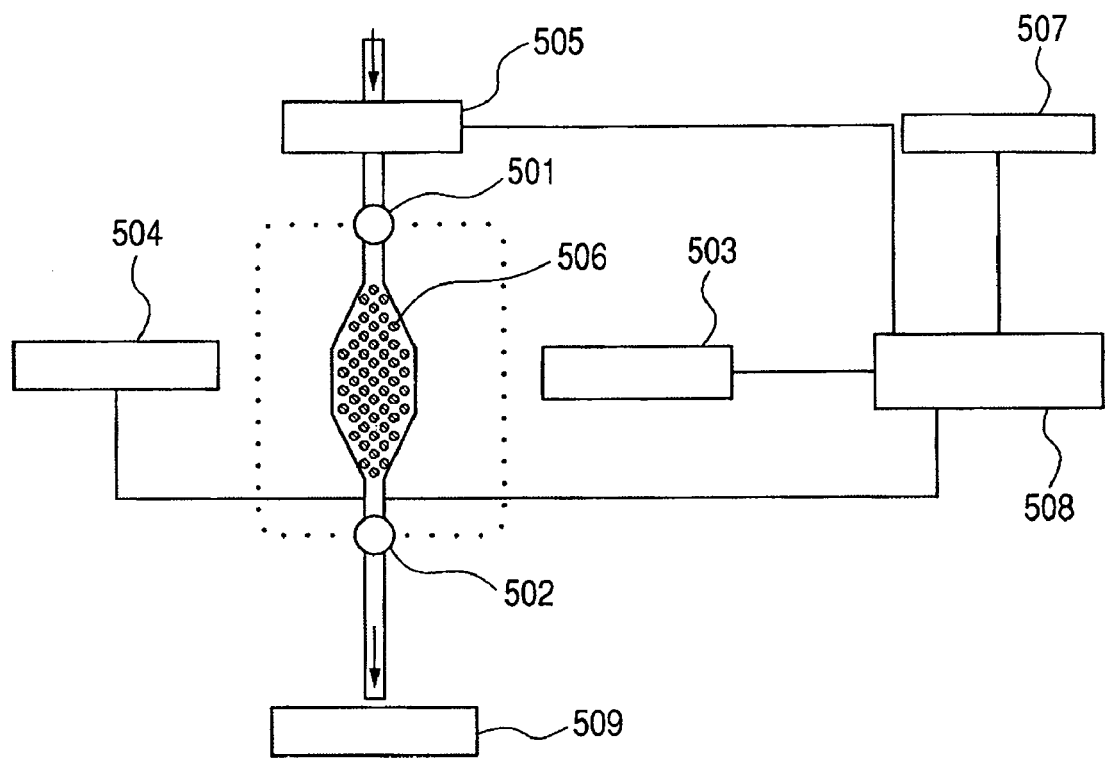
FIG. 5 is a block diagram showing a device using the target substance trapping chip of the present invention.

A detection method using the chip prepared above will be described. FIG. 5 is a block diagram showing a device using the chip and the chip. In the figure, the number of the reaction regions is one for simplification.

An inlet 501 and an outlet 502 are combined with the detection chip. The position of the detection chip (hereinafter may be called "chip") is adjusted so that the reaction region is on the optical axis between a spectrophotometer 503 and a light source 504. In this state, the spectrum before the reaction is detected using the spectrophotometer 503. Then, a pump 505 is driven to supply a predetermined amount of a sample to a reaction region of the detection chip 506, thereby causing an antigen-antibody reaction so that a target substance is trapped by the gold microparticles via an antibody. After the reaction, the spectrum is measured by the spectrophotometer 503. The spectrum of this time is compared with the spectrum before the reaction. The difference between them is the change in the localized surface plasmon resonance state of the gold microparticles caused by trapping a target substance in a region near the gold microparticles. The concentration of the target substance in accordance with the degree of the spectral change is determined and is displayed in a display unit 507. The reference numeral 508 denotes a central processing unit, and the reference numeral 509 denotes a waste liquid reservoir.

Here, the relation between the spectral change and the target substance concentration is obtained in advance using known standard samples with a plurality of concentrations. The calibration curve is determined based on this relation to determine the function between the spectral change and the concentration. Using this function, in an actual measurement, the concentration of a target substance with an unknown concentration can be determined based on the spectral change. The spectral change described herein may be a change in the spectral peaks at wavelengths including a maximum wavelength, may employ a change in the peak shape such as the peak width at half height of the spectral waveform, or may employ the light intensities at one or more wavelength points.

Example 2

Next, the detection device in Example 2 for detecting a target substance using luminescence by electrochemiluminescence, which employs a detection chip consisting of a composite with gold microparticles adsorbed on a projected structure made of ZnO, will be described.

Figure 6:
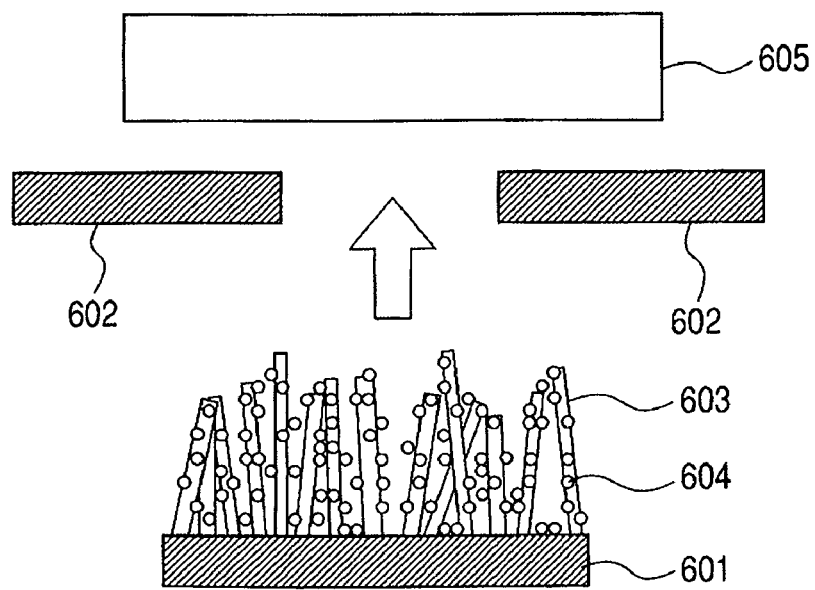
FIG. 6 is a view showing the configuration of the detection device in Example 2 of the present invention.

FIG. 6 is a schematic view in this example.

The detection chip is formed by a working electrode 601 formed with a transparent conductive film ITO layered on a glass substrate, a counter electrode 602 made of platinum, and composites each composed of a projected structure 603 and gold microparticles 604, and the space between the working electrode 601 and the counter electrode 602 can be filled with a liquid. In such a structure, reaction regions are formed each independently as required. Detection is carried out by a photoelectron multiplier tube (PMT) 605.

Here, a configuration in which reaction regions are located in a channel will be described with reference to FIGS. 7A, 7B and 7C.

Figure 7A:
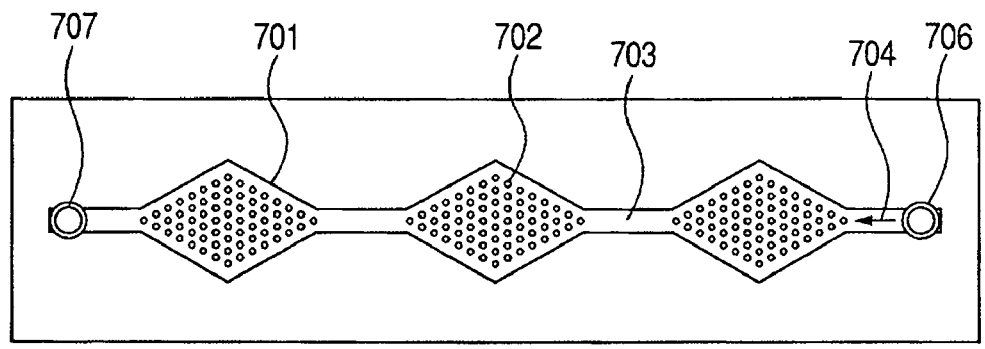
FIGS. 7A, 7B and 7C are other views showing the configuration of the detection device in Example 2 of the present invention.
Figure 7B:
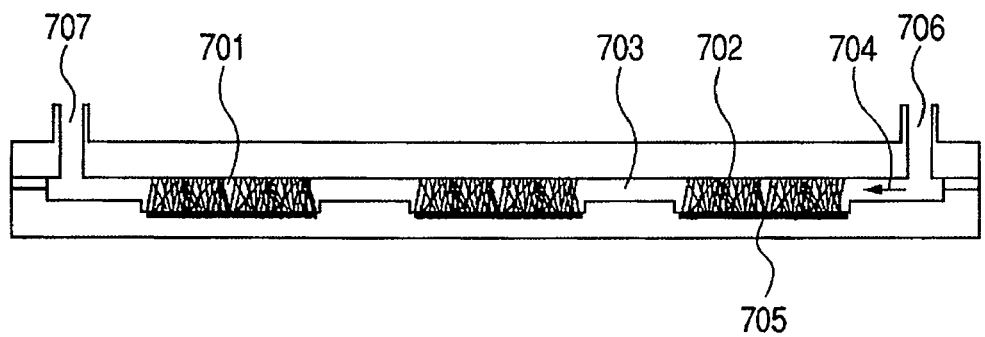
Figure 7C:
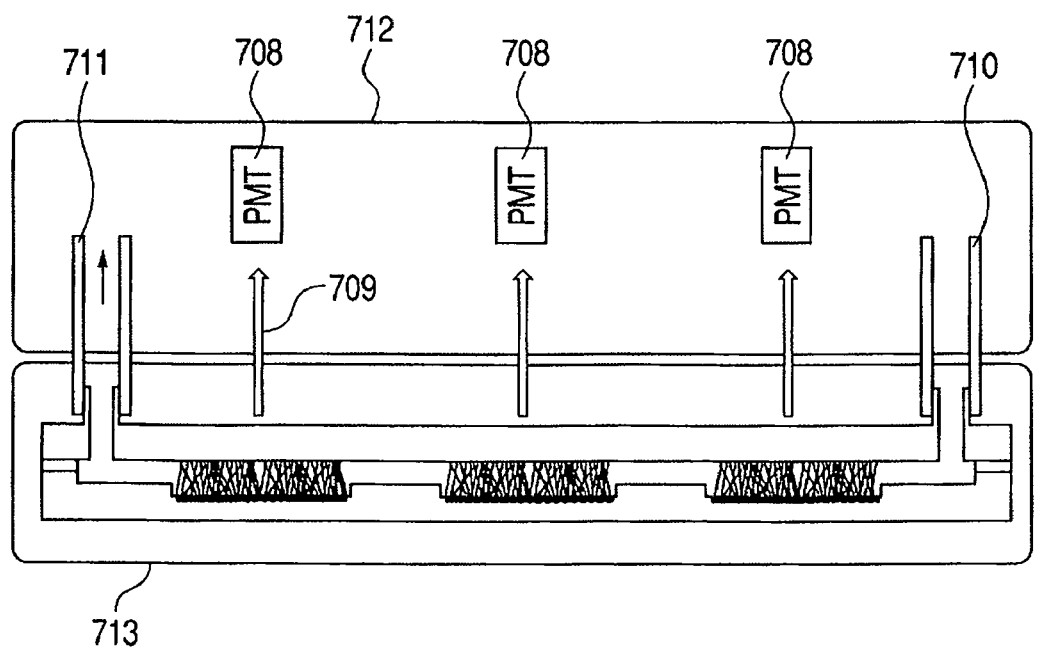

FIG. 7A is a view of a detection chip from the top surface, and FIG. 7B is a side view of the chip. A plurality of reaction regions 701 are located in a channel 703. In each of the reaction regions 701, a composite 702 composed of a projected structure and gold microparticles are formed. At the bottom of the projected structure, a counter electrode 705 is formed. A sample 704 is introduced into an inlet 706, passes through the reaction regions 701 and is discharged from an outlet 707. FIG. 7C is a side view when a detection device 712 is combined with a detection chip 713. In the configuration, the inlet and the outlet are connected with a sample inlet connector 710 and a sample outlet connector 711, respectively, and the sample is introduced into the connector 710 and discharged from the connector 711. Luminescence 709 by electrochemiluminescence from each reaction region is detected by a photoelectron multiplier tube 708.

A plurality of reaction regions in the chip can trap and detect a plurality of substances to be detected at the same time from one sample. In addition, since a channel is used when introducing a sample or a reagent or lavage for detection into a reaction region using a microstructure, reaction, detection and cleaning treatments can be carried out with more stable quantitativeness and reproducibility.

<Method for Preparing Target Substance Trapping Tip>

First, a projected structure made of ZnO is prepared using a method disclosed in Japanese Patent Application Laid-Open No. 2002-167300. As a substrate on which the projected structure is fixed, a glass plate with ITO as a transparent conductive film layered thereon is used. The projected structure made of ZnO is combined with gold microparticles as follows. The projected structure made of ZnO is immersed in a solution of aminoethanethiol, having a thiol group to be bonded to a metal oxide, in ethanol. Next, the projected structure is immersed in an aqueous solution of gold microparticles with a particle diameter of 20 to 40 nm each (manufactured by Tanaka Kikinzoku Kogyo K.K.) to prepare a composite in FIG. 6 in which the gold microparticles are adsorbed on the surface of the projected structure 604.

Next, a method of fixing an anti-AFP (a-fetoprotein) antibody as a target substance trap used in this example on the surface of the gold microparticles will be exemplified. The surface of the gold microparticles is modified using a solution of 11-mercaptoundecanoic acid, with a thiol group having a high affinity to gold, in ethanol. In this case, a predetermined amount of the solution is added dropwise to only the reaction region using a spotter or the like. A carboxyl group is thus exposed on the surface of the gold microparticles. In this state, an aqueous solution of N-hydroxysulfosuccinimide (manufactured by Dojindo Laboratories) and an aqueous solution of 1-ethyl-3-[3-dimethylamino]propyl]carbodiimide hydrochloride (manufactured by Dojindo Laboratories) are added dropwise to the reaction region using a spotter in the same manner. A succinimide group is thus exposed on the surface of the gold microparticles. Further, the surface of the gold microparticles is modified with streptavidin by bonding streptavidin thereto. A biotinylated anti-AFP antibody is fixed on the gold microparticles.

It is obviously possible to provide a configuration in which different antibodies are respectively fixed on a plurality of reaction regions and different target substances are detected by one chip. This configuration is achieved by carrying out the same procedure as in the above method using different antibodies.

<Detection Method>

Luminescence by electrochemiluminescence is confirmed after the following process.

(1) a sample comprising AFP as a target substance is flown into the prepared chip to cause AFP to be trapped on the microparticles.

(2) The sample is drained, and the channel is washed with a phosphate buffer.

(3) An anti-AFP monoclonal antibody labeled with Ru(II) $(bpy)_3^{2+}$ is caused to be adsorbed on the chip.

(4) The labeled antibody solution is drained, and the channel is washed with a phosphate buffer.

AFP as an antigen and the anti-AFP monoclonal antibody labeled with $Ru(II)(bpy)_3^{2+}$ are thus trapped by the chip. Here, in order to cause electrochemiluminescence, a space between the working electrode and the counter electrode is filled with a TPA (tripropylamine) solution as an electron donating substance, and the electrodes are charged. Electrochemiluminescence due to ruthenium on the solid phase bonded to the electrode surface and TPA in the cells thus occurs, and the luminescence is measured at PMT605. This luminescence intensity depends on the amount of Ru(II) $(bpy)_3^{2+}$ trapped. Specifically, since the luminescence intensity depends on the amount of AFP trapped, the concentration of AFP can be determined. The relation between the luminescence intensity and the AFP concentration in the sample is determined using an AFP control solution at a known concentration in advance.

Example 3

The detection device in Example 3 using a convex structure as a microstructure will be described below with reference to FIG. 8.

<Configuration>

The detection device in this example is configured by a laser diode light source 801, a collimator lens 802, a detection chip 804 consisting of a composite of a convex structure and gold microparticles 805, a collimator lens 807, a filter 808 and a photoelectron multiplier tube 809.

<Method for Preparing Target Substance Trapping Tip>

Here, as a method for preparing a convex structure, a technique disclosed in Japanese Patent Application Laid-Open No. 2000-263556 is adopted. A microlens array made of $SiO_2$ with a shape in FIG. 2E is manufactured by this method. In order to make the gold microparticles adsorbed on the surface of the microlens array, the lens surface is first treated with an aminosilane coupling agent (manufactured by Chisso Corporation) so that an amino group appears on the surface. This microarray lens is immersed in a solution of gold microparticles with a particle diameter of 20 to 40 nm each (manufactured by Tanaka Kikinzoku Kogyo K.K.) to give a composite with a surface on which gold microparticles are adsorbed. Next, the same method as in Example 2 is used for causing streptavidin to adhere to the surface of the gold microparticles. Finally, an anti-CEA antibody, anti-AFP antibody, anti-PSA antibody and anti-PAP antibody that are modified with biotin are adsorbed thereon to provide the target substance trapping chip of the present invention.

<Detection Method>

In FIG. 8, light from the laser diode light source 801 is converted into parallel light 803 by the collimator lens 802. The composite 804 of the convex structure and the gold microparticles 805 is irradiated with the parallel light 803. In order to prevent detection of reflected light 806 from the composite 804, the filter 808 for blocking light within the wavelength range of the incident light is inserted immediately in front of the photoelectron multiplier tube 809. Fluorescence emitted from a fluorescence pigment fixed on the gold microparticles 805 passes through the collimator lens 807 and is detected by the photoelectron multiplier tube 809 via the filter 808.

In an actual measurement, detection of various antigens of CEA, AFP, PSA and PAP known as markers for cancers is attempted. The various antigens are caused to bind specifically to antibodies in the following procedure.

(1) Samples each containing a CEA antigen, AFP antigen, PSA antigen or PAP antigen solution are introduced into the channel and incubated for five minutes.

(2) The antigen solutions are drained, and the channel is washed with a phosphate buffer.

(3) an anti-CEA antibody, anti-AFP antibody, anti-PSA antibody and anti-PAP antibody that are fluorescence labeled with a Cy5 pigment are each introduced into the channel and incubated for five minutes.

(4) The labeled antibodies are drained, and the channel is washed with a phosphate buffer.

(5) The channel is filled with a phosphate buffer.

By introducing a laser beam after this process, fluorescence from the gold microparticles on the microlens array can be observed. Since the fluorescence intensity differs according to the concentration of the fluorescence pigment, the concentration dependency of the target substances can be detected.

Example 4

The detection device in Example 4 in which a column microstructure is used as a microstructure instead of the convex structure in Example 3 will be described with reference to FIG. 10.

When the detection chip with a column structure in this example is compared with the detection chip with a hollow structure having the same dimensions as in the column structure, it is found that the reaction time in the hollow structure depends on the pore diameter, and the reaction time in the column structure depends on the interval between the columns. Although the cross-section of the channel for introducing a sample in the hollow structure has a cross-section of pores, the channel in the column structure has a cross-section of intervals between the columns. This makes it easy to design the column structure taking channel resistance into consideration.

The detection device in this example is the same as that in Example 3. Specifically, as shown in FIG. 10, the detection device is configured by a laser diode light source 1, a collimator lens 2, a detection chip consisting of a composite of a column structure 4 and gold microparticles 5, a collimator lens 7, a filter 8 and a photoelectron multiplier tube 9.

Figure 10:
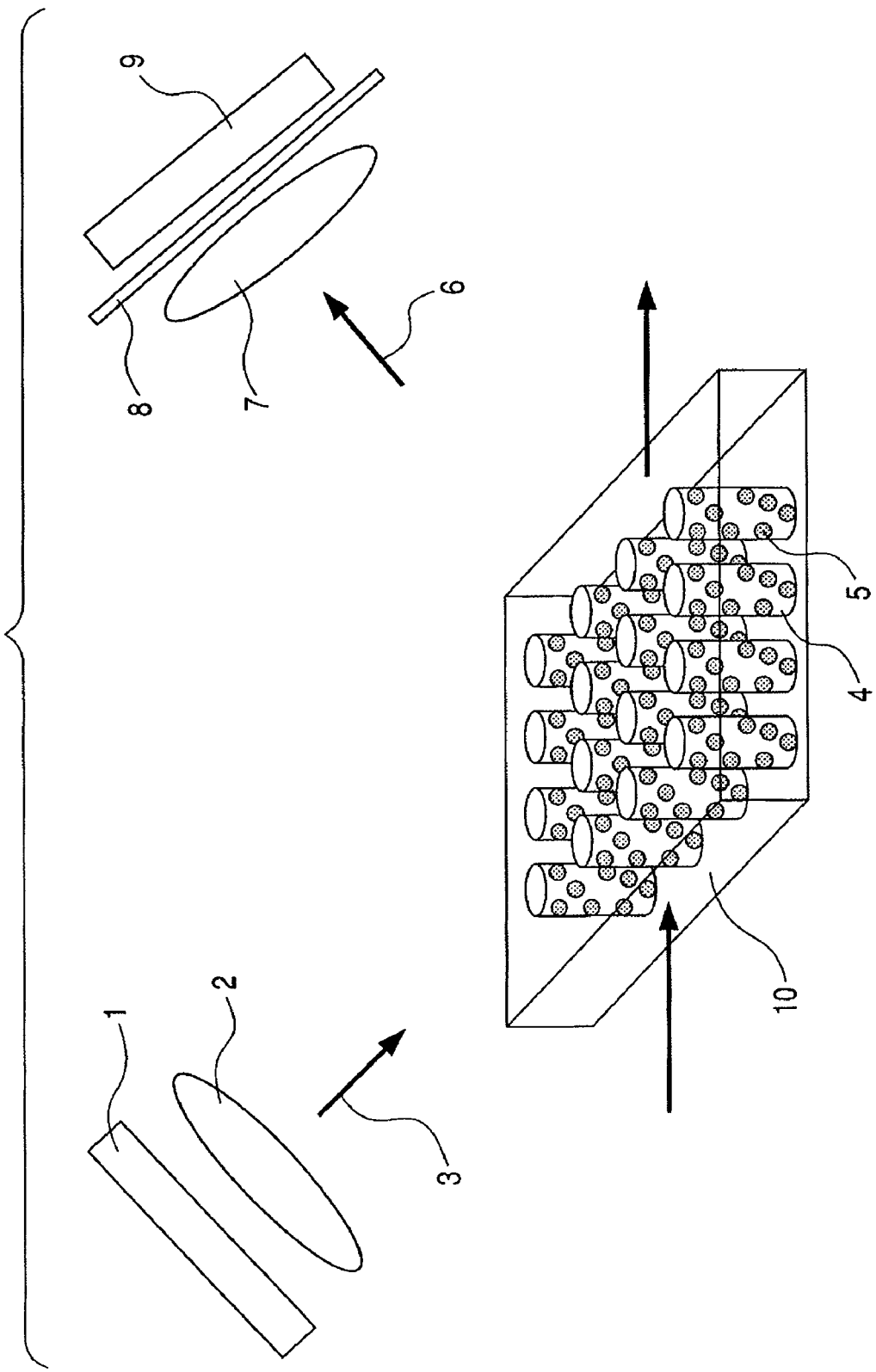
FIG. 10 is a view showing the configuration of the detection device in Example 4 of the present invention.

In FIG. 10, light from the laser diode light source 1 is converted into parallel light 3 by the collimator lens 2. The composite formed in a channel 10 of the column structure 4 and the gold microparticles 5 is irradiated with the parallel light 3. In order to prevent the photoelectron multiplier tube 9 from detecting reflected light from the composite, the filter 7 for blocking light within the wavelength range of the incident light is inserted immediately in front of the photoelectron multiplier tube 9. Since fluorescence 6 as luminescence from a fluorescence pigment fixed on the gold microparticles 5 has a wavelength differing from that of the incident light 3, the fluorescence is detected by the photoelectron multiplier tube 9 via the filter 8.

Figure 11:
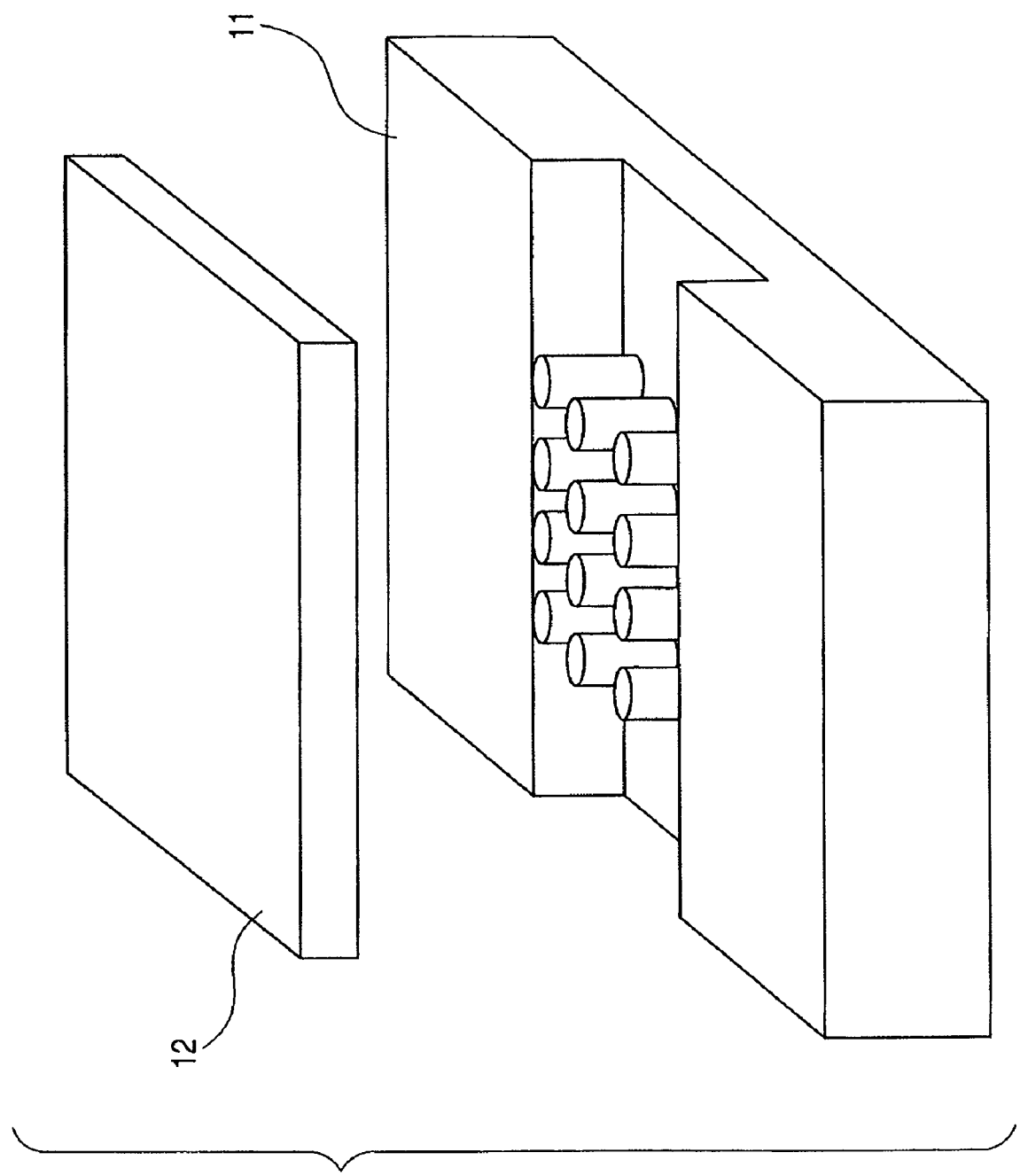
FIG. 11 is another view showing the configuration of the detection device in Example 4 of the present invention.

The channel 10 and the column structure as a microstructure formed in the channel 10 are manufactured as follows. As shown in FIG. 11, a silicon substrate is dry-etched to give a groove and a silicon substrate 11 in which the column microstructure is formed in the groove. As a manufacturing method of giving a column microstructure by dry etching a silicon substrate, high vacuum plasma etching disclosed in U.S. Pat. No. 6,531,068 that enables deep etching by repeating deposition and etching has been used. Thus, a groove and a microstructure in the groove consisting of a column microstructure with any shape and arrangement can be formed in a silicon substrate. As described later, after a target substance trap is fixed on the surface of the column structure, the silicon substrate 11 is attached to a PDMS resin substrate 12, so that a channel for causing a sample to flow can be formed.

Etching was carried out using a photoresist formed by a conventional photolithography as a mask under the following conditions to form a 100 μm-wide and 20 μm-deep groove and groups of cylinders in the groove, each consisting of cylinders within a 1 cm-long region, at the same intervals between the groups. The cylinders have a diameter of 3 μm and a height of 20 μm each, and are separated with each other at an interval of 1 μm. The height of each cylinder is almost the same as the depth of the groove. The diameter and the arrangement in the groove of the cylinders may be arbitrarily selected according to the design of the mask pattern.

Etching Conditions

Figure 12A:
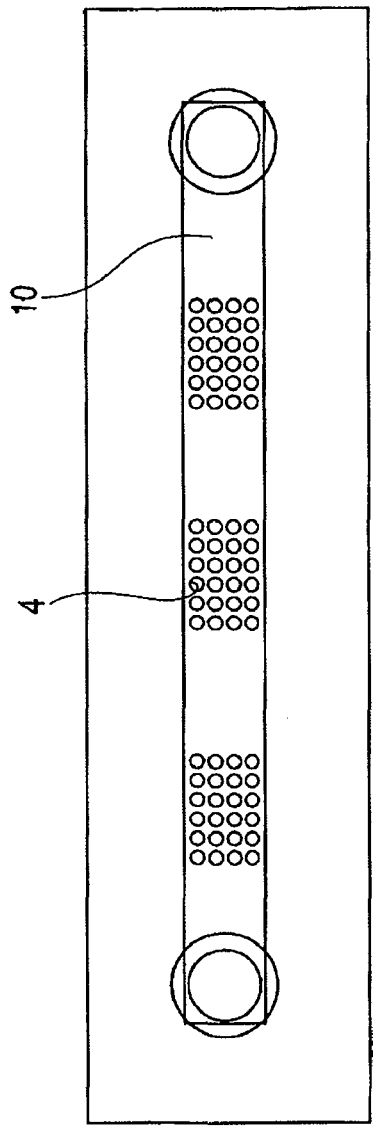
FIGS. 12A and 12B are views showing the configuration of the detection device in Example 4 of the present invention.
Figure 12B:
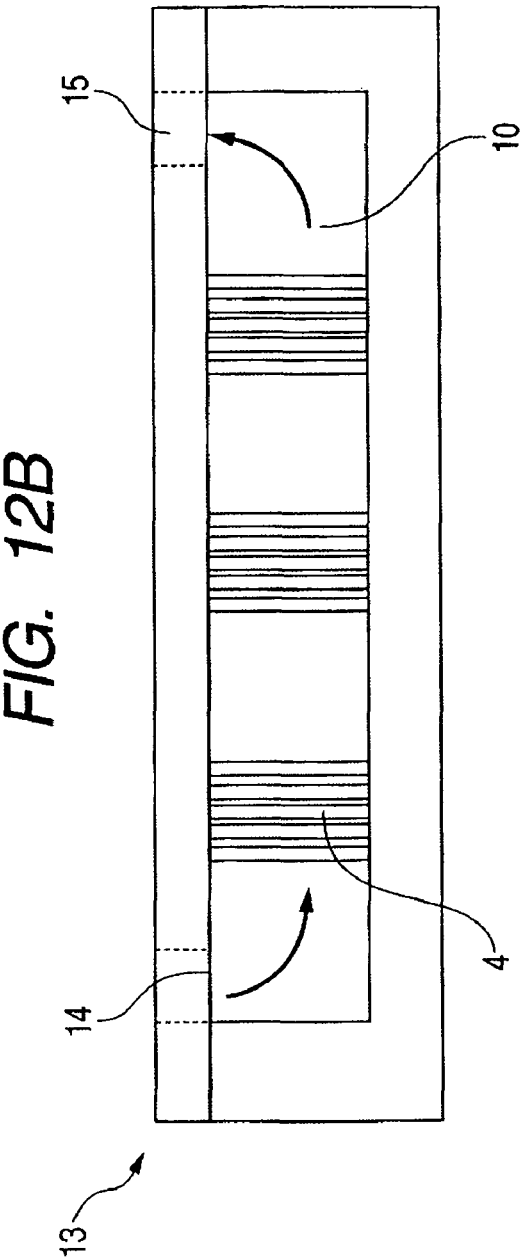

Deposition Conditions
  Pressure: 0.133 Pa
  100 sccm $C_4F_8$
  800 W 13.56 MHz
  5 seconds Etching Conditions
  Pressure: 0.266 Pa
  130 sccm high frequency 100 sccm $C_4F_8$
  13.56 MHz
  9 seconds An arrangement of a column structure in a channel makes it possible to trap and detect a plurality of substances to be detected at the same time in one chip. For example, as shown in FIGS. 12A and 12B, if three regions of column structure are formed and three different target substances are fixed on the respective regions, three different substances to be detected can be trapped and detected at the same time. It is obvious that the dimension and arrangement can be appropriately designed according to the substance to be detected.

The gold microparticles are fixed on the column structure in the channel as in Example 3. An amino group is exposed on the surface of the column structure by an aminosilane coupling agent (manufactured by Chisso Corporation), and is reacted with an aqueous solution of gold microparticles with a particle diameter of 20 to 200 nm each (manufactured by BBInternational Ltd.) to give a composite with a surface on which the gold microparticles are fixed. Next, the surface of the gold microparticles is modified with streptavidin by a thiol in the same manner as in Example 2. The surface of the gold microparticles is reacted with a biotinylated anti-troponin T antibody to fix the antibody as a target substance trap thereon.

Next, measurement was carried out using a detection chip shown in FIGS. 12A and 12B.

In the detection chip 13 in FIGS. 12A and 12B, the above PDMS resin substrate 12 is attached to the silicon-substrate 11 having a groove as the channel 10 in which the column structure 4 is formed. In the PDMS resin substrate 12, an inlet 14 is formed in the part corresponding to one end of the groove formed in the silicon substrate, and an opening as an outlet 15 is formed at the position corresponding to the other end of the groove.

Detection of troponin T known as a marker for acute myocardial infarction will be explained as an example. Troponin T as an antigen is caused to bind specifically to an antibody in the following procedure.

(1) A troponin T antigen solution is introduced from the inlet 14 in FIGS. 12A and 12B into the channel 10, and incubated for five minutes.

(2) The antigen solution is drained, and the channel is washed with a phosphate buffer.

(3) an anti-troponin T antibody that is fluorescence labeled with a Cy5 pigment is introduced from the inlet 10 into the channel and incubated for five minutes.

(4) The labeled antibody is drained, and the channel is washed with a phosphate buffer.

(5) The channel is filled with a phosphate buffer.

By irradiating the reaction region with excitation light from the laser diode light source in FIG. 10 after this process, fluorescence from the surface of the gold microparticles can be observed. Since the fluorescence intensity differs according to the concentration of the fluorescence pigment, the concentration dependency of the target substances can be quantitatively determined.

Example 5

In this example, a silica porous thin film with pores having a diameter of 10 nm each was formed on a glass substrate, gold microparticles were formed in the pores, and a target substance trap was stabilized and held in the pores to detect a target substance.

FIGS. 13A and 13B are schematic views showing the structure of a detection chip 13 used in this example. As shown in the figures, a PDMS substrate with a groove as a channel 10 formed is attached to a PDMS substrate 18 covering the channel 10 to form the detection chip. In the PDMS substrate 18 covering the channel 10, an inlet 14 is formed in the part corresponding to one end of the groove as the channel 10, and an opening as an outlet 15 is formed at the position corresponding to the other end of the groove.

At the bottom of the groove as the channel 10, a glass substrate 17, on which a porous thin film 16 with a surface supporting gold microparticles 5 is formed, is located.

The method for manufacturing the glass substrate 17 with a surface on which the porous thin film 8 is formed and the method for causing the porous thin film 16 to support the gold microparticles 5 will be described below.

First, the surface of the glass substrates was washed with isopropyl alcohol and pure water, and irradiated with UV in an ozone generator to clean the surface.

Next, 0.5 g of a triblock copolymer F127 ($HO(CH_2CH_2O)_{106}(CH_2CH(CH_3)O)_{70}(CH_2CH_2O)_{106}H$) (manufactured by BASF) was dissolved in 20 g of ethanol. Then, 4.16 g of tetraethoxysilane (TEOS), 1.0 g of water and 0.81 g of 0.1 M hydrochloric acid were added, and the mixture was stirred at room temperature for two hours to prepare a reaction solution.

The reaction solution was applied to the glass substrate by dip coating, and dried in an atmosphere at 25° C. at a relative humidity of 50% for 24 hours. The pulling rate was 3 cm/min.

Then, the substrate was put in a muffle furnace, heated to 450° C., and sintered in air for five hours. The substrate was observed after sintering to confirm that an uniform and continuous thin film was formed.

Next, the surface and cross-section of the thin film were observed by SEM to confirm based on the surface observation that there were spherical pores with a diameter of 10 nm each. Based on the surface observation, there were oval pores shrunken in the film thickness direction observed, with a longitudinal diameter of 12 nm and a latitudinal diameter of 5 nm.

Next, an X-ray diffraction analysis was carried out to observe a distinct diffraction peak attributed to a cubic pore structure at an angle corresponding to a spacing of 7.5 nm. However, an SEM observation of the cross-section and the like confirmed that the thin film actually has a cubic structure shrunken in the film thickness direction.

The above results confirmed that a porous thin film with a pore diameter of 10 nm each was formed on a glass substrate.

Next, gold microparticles were caused to be supported in the pores of the porous thin film.

First, the substrate with the porous thin film formed thereon was immersed in an aqueous solution of tetrachloro-gold(III) acid trihydrate (0.1 g/20 ml), and allowed to stand for 24 hours. The substrate was then immersed for 10 minutes, and the surface was washed with dichloromethane and dried at room temperature. The reduction treatment was then carried out. The reduction treatment was carried out by holding the glass substrate with the porous thin film formed thereon in a tube furnace, charging the furnace with a hydrogen/helium mixed gas at a hydrogen concentration of 2% at 50 ml/min, and heating the substrate at 120° C. for three hours.

A TEM observation after the reduction treatment confirmed that the pore structure was maintained and the gold microparticles were formed in the pores.

Next, the surface of the gold microparticles is modified with streptavidin by a thiol in the same manner as in Example 2. The surface of the gold microparticles is reacted with a biotinylated anti-PSA antibody to fix the antibody as a target substance trap thereon.

Figure 9A:
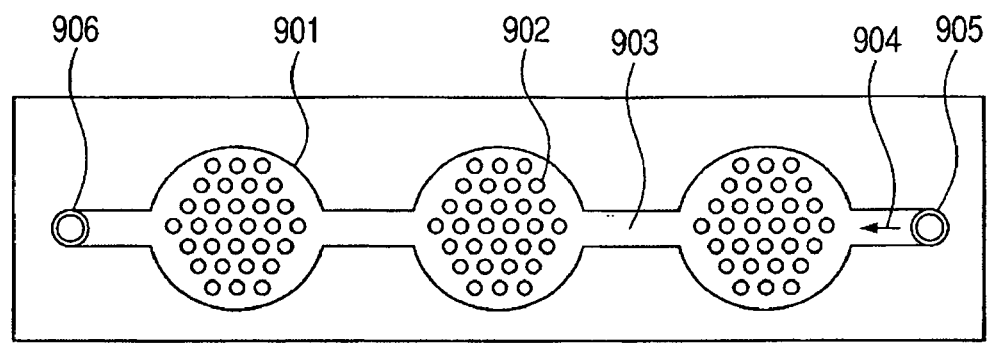
FIGS. 9A, 9B and 9C are respectively another view showing the configuration of the detection device in Example 3 of the present invention.
Figure 9B:
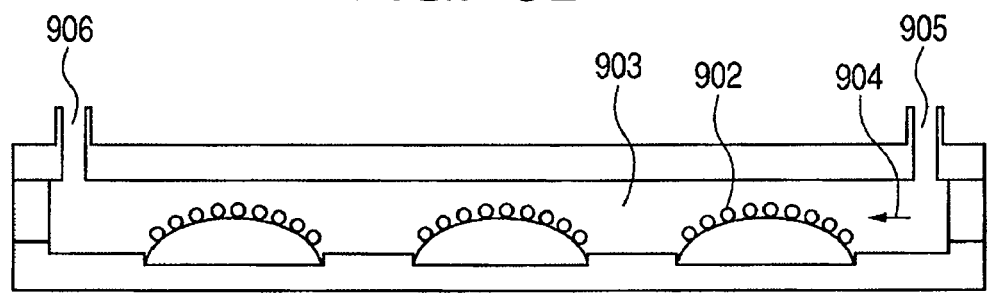
Figure 9C:
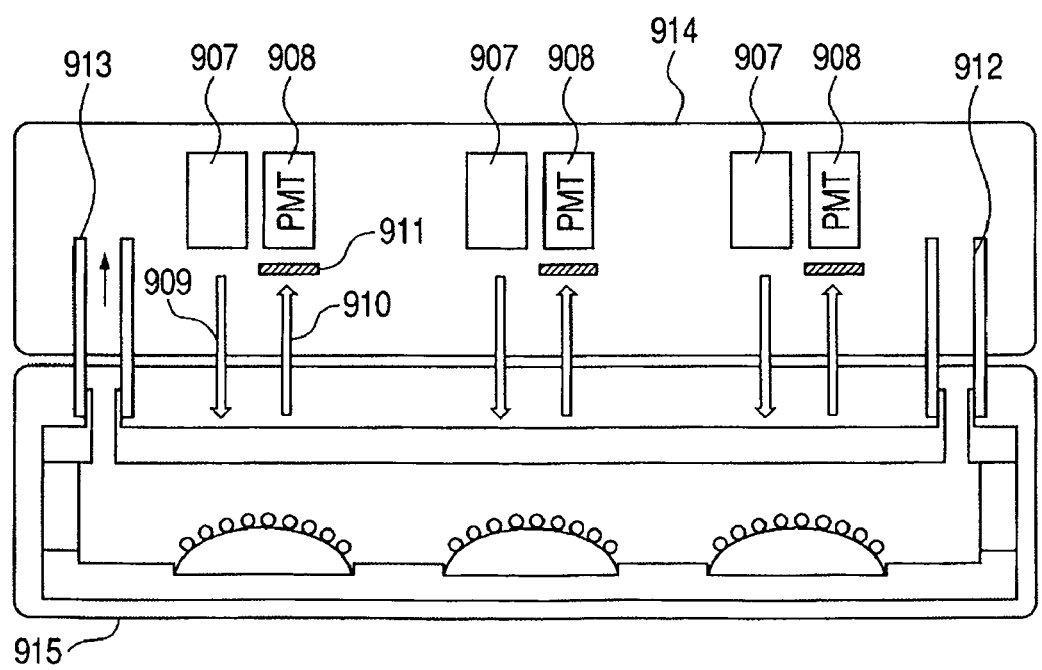

Detection of PSA known as a marker for prostate cancer using the detection chip in FIGS. 13A and 13B will be explained as an example. PSA as an antigen is caused to bind specifically to an antibody in the following procedure. The same optical system for detection as in FIGS. 8, 9A, 9B and 9C in Example 3 can be used. In FIGS. 9A, 9B and 9C, the reference numeral 901 denotes a reaction region, the reference numeral 902 denotes metal element-containing microparticles, the reference numeral 903 denotes a channel, the reference numeral 904 denotes a sample, the reference numeral 905 denotes an inlet, the reference numeral 906 denotes an outlet, the reference numeral 907 denotes a laser diode, the reference numeral 908 denotes a photoelectron multiplier tube (PMT), the reference numeral 909 denotes excitation light, the reference numeral 910 denotes fluorescence, the reference numeral 911 denotes a filter, the reference numeral 912 denotes a sample inlet connector, the reference numeral 913 denotes a sample outlet connector, the reference numeral 914 denotes a detection device, and the reference numeral 915 denotes a detection chip.

(1) a PSA antigen solution is introduced from the inlet 14 into the channel and incubated for five minutes.

(2) The antigen solution is drained, and the channel is washed with a phosphate buffer.

(3) an anti-PSA antibody that is fluorescence labeled with a Cy5 pigment is introduced from the inlet 14 into the channel in FIGS. 13A and 13B, and incubated for five minutes.

(4) The labeled antibody is drained, and the channel is washed with a phosphate buffer.

(5) The channel is filled with a phosphate buffer.

By introducing the excitation light from the laser diode light source into the reaction region after this process, fluorescence from the surface of the gold microparticles can be observed. Since the fluorescence intensity differs according to the concentration of the fluorescence pigment, the concentration dependency of the target substances can be quantitatively determined.

The present invention should not be limited to the above-described examples. It is obvious that combinations of these examples and modifications within the spirit of the present invention are possible.

This application claims priorities from Japanese Patent Application Nos. 2004-062606 filed on Mar. 5, 2004, and 2004-188879 filed on Jun. 25, 2004, which are hereby incorporated by reference herein.

The invention claimed is:

1. A detection device comprising:
   a microstructure as a channel for transporting a sample, the microstructure comprising: a plurality of voids each having a diameter of 1 nm to 10 μm; and a plurality of microparticles of which properties are changed due to contact with a target substance, the plurality of microparticles containing a metal element and being provided on a surface of the plurality of voids,
   means for bringing the target substance into contact with the plurality of microparticles; and
   means for detecting a change in properties of the plurality of microparticles caused when the target substance is brought into contact with the plurality of microparticles, based on light transmitted through the microstructure when the plurality of microparticles are irradiated with light,
   wherein the plurality of microparticles are located in a direction in which the light for irradiating the microstructure travels, and
   wherein the detecting means is a means for detecting the change in the properties of the plurality of microparticles based on a summation of light output from the plurality of microparticles upon irradiation with light.

2. The detection device according to claim 1, wherein the plurality of microparticles further comprise a trap for trapping the target substance on the surface, and the target substance is trapped in the trap.

3. The detection device according to claim 1, wherein the detecting means detects the change in the properties by detecting plasmon resonance.

4. A detection method comprising the steps of:
   providing a microstructure as a channel for transporting a sample, the microstructure comprising: a plurality of voids each having a diameter of 1 nm to 10 μm; and a plurality of microparticles of which properties are changed due to contact with a target substance, the plurality of microparticles containing a metal element and being provided on a surface of the plurality of voids;

bringing the target substance into contact with the plurality of microparticles; and detecting a change in properties of the plurality of microparticles caused when the target substance is brought into contact with the plurality of microparticles in the contact step, based on light transmitted through the microstructure when the plurality of microparticles are irradiated with light, wherein the detecting step comprises a detection based on a summation of light output from the plurality of microparticles located in a direction in which the light for irradiation travels.

5. A detection chip comprising:

a microstructure as a channel for transporting a sample, the microstructure comprising: a plurality of voids each having a diameter of 1 nm to 10 μm; and a plurality of microparticles of which properties are changed due to contact with a target substance, the plurality of microparticles containing a metal element and being provided on a surface of the plurality of voids; and means for bringing the target substance into contact with the plurality of microparticles, wherein a change in properties of the plurality of microparticles caused when the target substance is brought into contact with the plurality of microparticles is detected based on light transmitted through the microstructure when the plurality of microparticles are irradiated with light, and the plurality of microparticles are located in a direction in which the light for irradiating the microstructure travels.

* * * * *